United States Patent [19]
Blanch et al.

[11] Patent Number: 5,844,142
[45] Date of Patent: Dec. 1, 1998

[54] PULL TEST APPARATUS FOR PERMANENTLY ATTACHED SUTURES

[75] Inventors: John F. Blanch, Tinton Falls; Anthony Esteves, Somerville; David D. Demarest, Parsippany, all of N.J.

[73] Assignee: Ethicon, Inc., Somerville, N.J.

[21] Appl. No.: 847,132

[22] Filed: Apr. 30, 1997

[51] Int. Cl.$^6$ ..................................................... G01N 3/10

[52] U.S. Cl. ............................................. 73/827; 73/833

[58] Field of Search ............................ 73/827, 830, 831, 73/834, 833; 29/517

[56] References Cited

U.S. PATENT DOCUMENTS

| | | | |
|---|---|---|---|
| 5,438,746 | 8/1995 | Demarest et al. | 29/517 |
| 5,485,668 | 1/1996 | Demarest et al. | 29/517 |
| 5,487,308 | 1/1996 | Demarest et al. | 73/827 |
| 5,500,991 | 3/1996 | Demarest et al. | 29/517 |

*Primary Examiner*—Max H. Noori

[57] ABSTRACT

A semi-automated machine for singulating individual surgical needles from an bulk supply and attaching a suture to the surgical needle is described. Each of the surgical needles has a suture receiving opening formed therein for receiving a suture. The machine includes a needle singulation station, a precise positioning station, a suture feeding station, a swage station, a pull-test station and an off-load station. A universal gripper mounted on a rotary indexing device automatically receives each individual needle in a predetermined orientation and conveys the needle for sequential processing from station to station to form the needle-suture assembly. A swage station is provided for swaging the needle to close the suture receiving opening about the suture to secure said suture thereto and form therefrom a needle and suture assembly. The suture pull-test station tests each needle suture bond with a pre-determined pull for quality control. This pull is adjustable via a precision spring tension device. The pull test station includes two sets of jaws for gripping the suture, the first for the quality control pull test, and the second for a destructive test in which the strength of the bond is measured for adjusting the swage dies and for statistical quality control purposes. A final off-load station provides an apparatus for assembling a predetermined number of need-suture assemblies in a bundle for subsequent packaging.

26 Claims, 29 Drawing Sheets

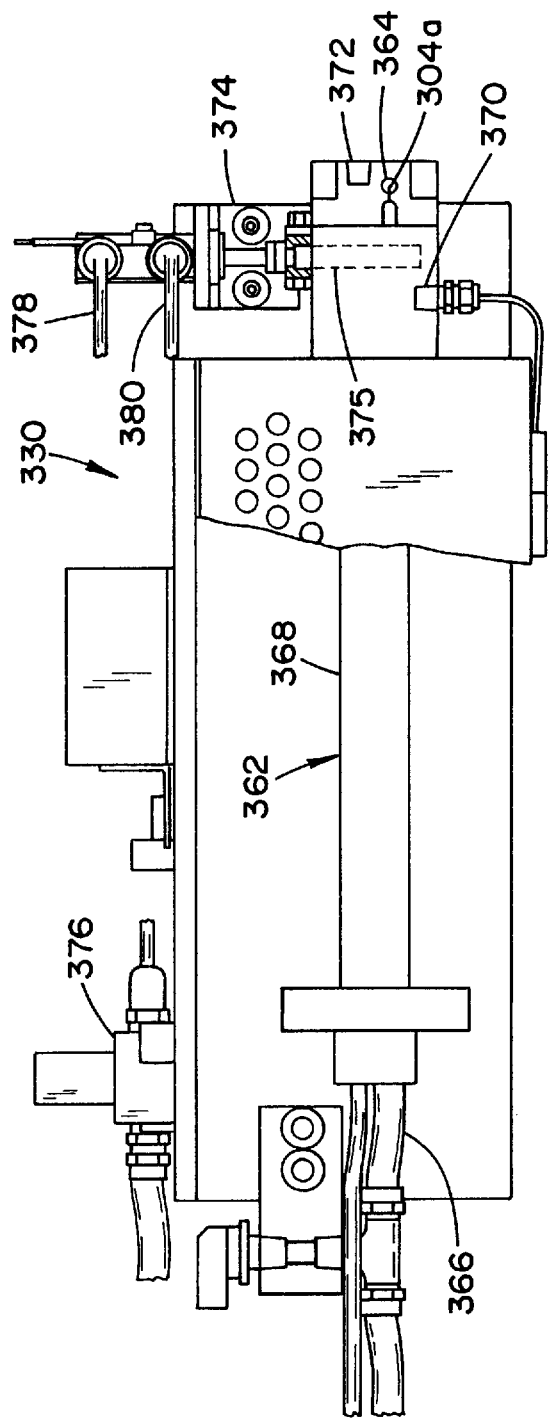

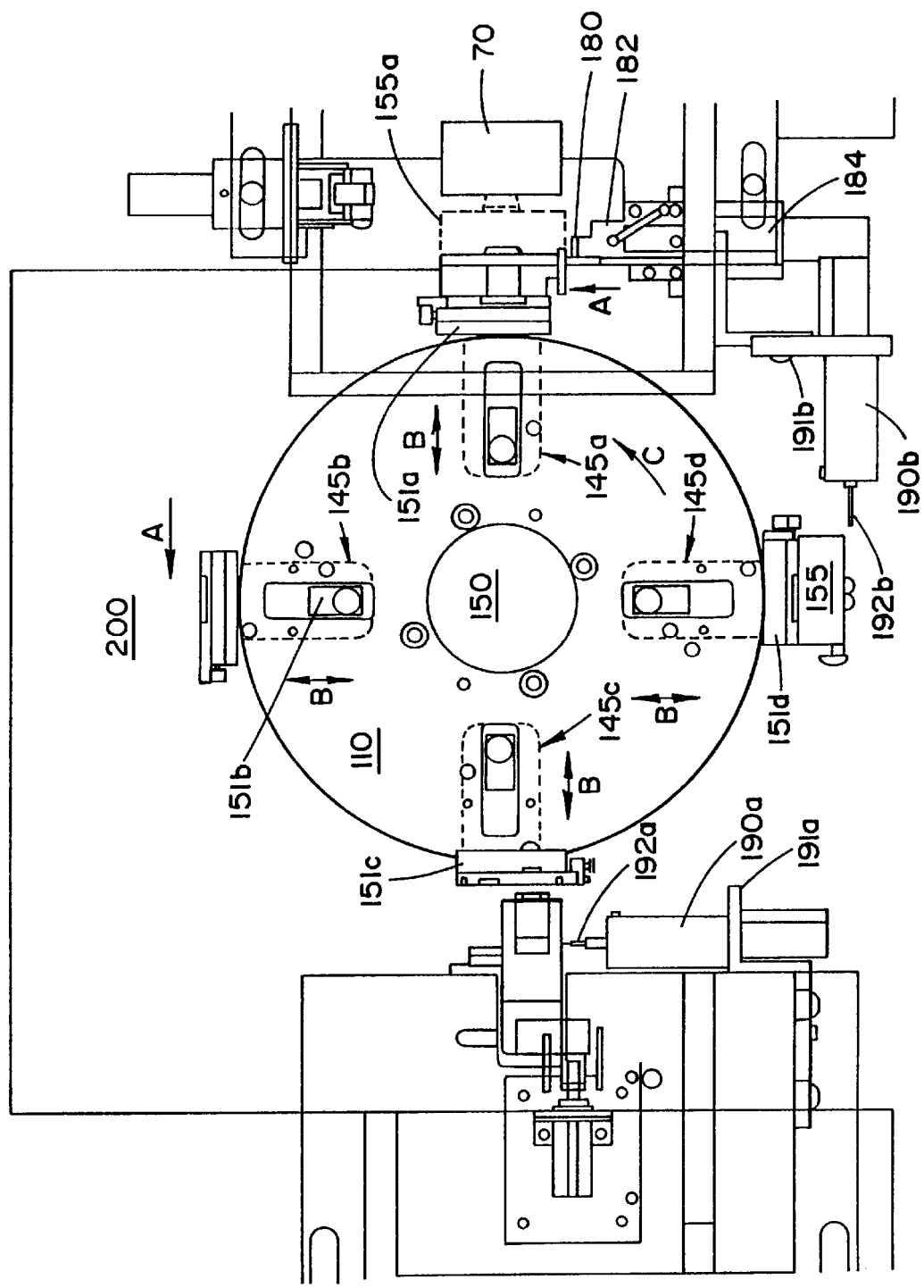

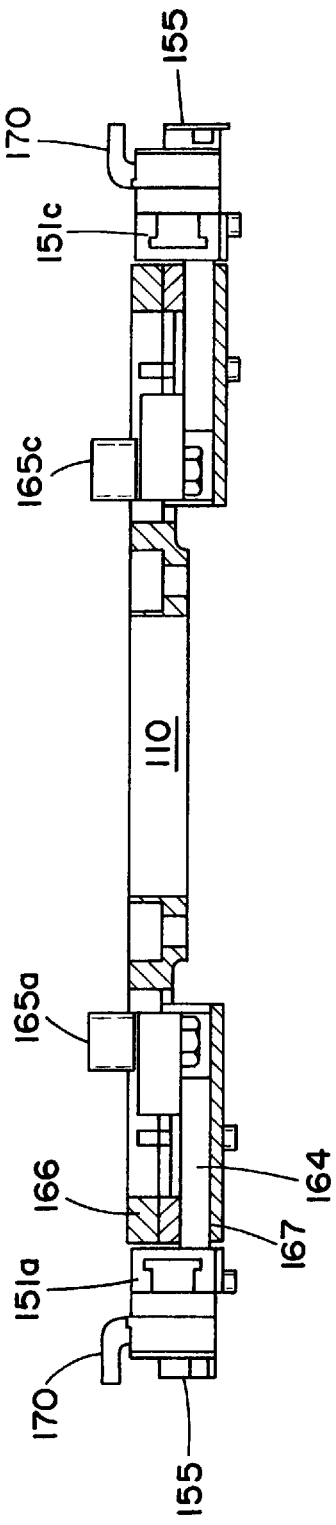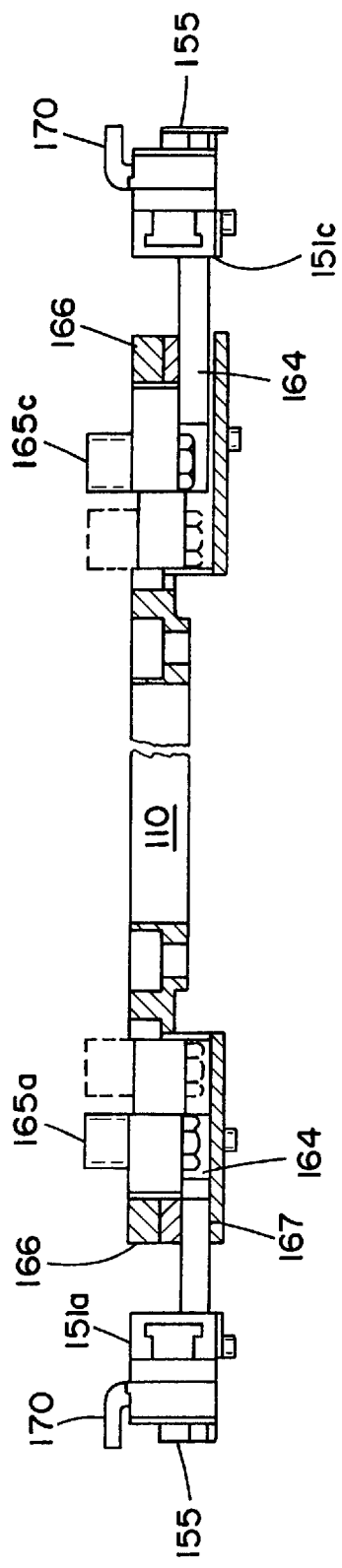

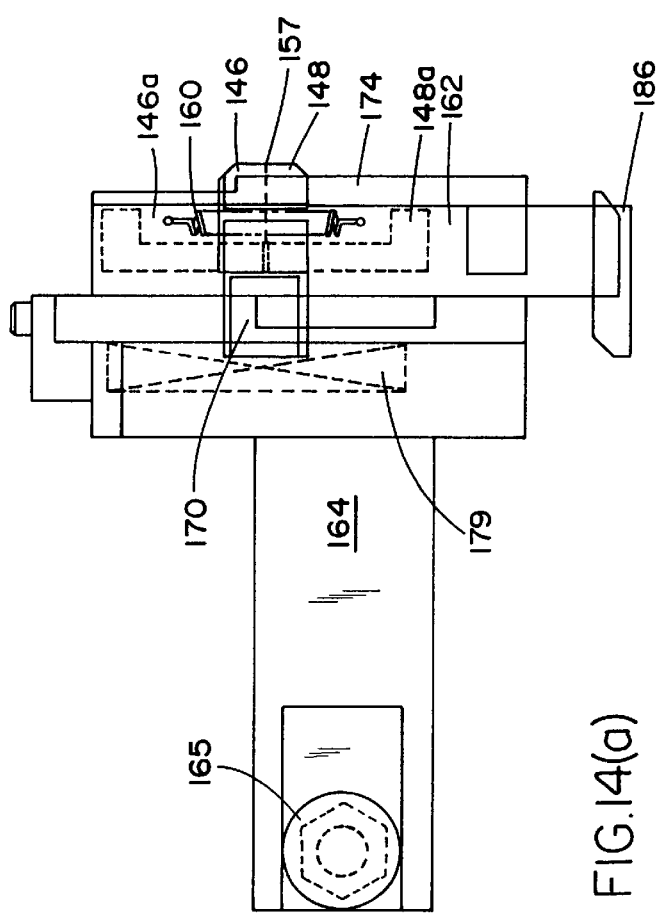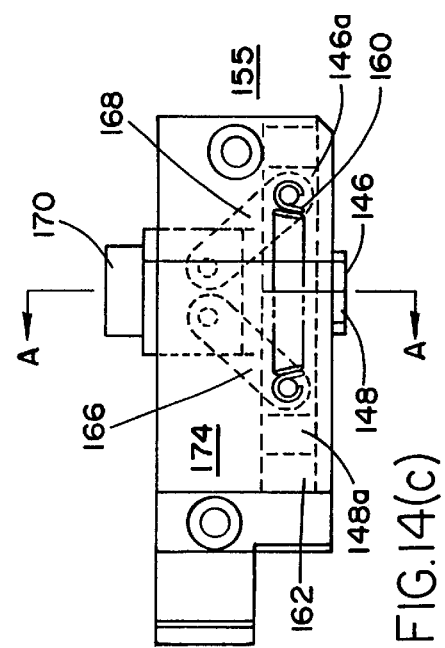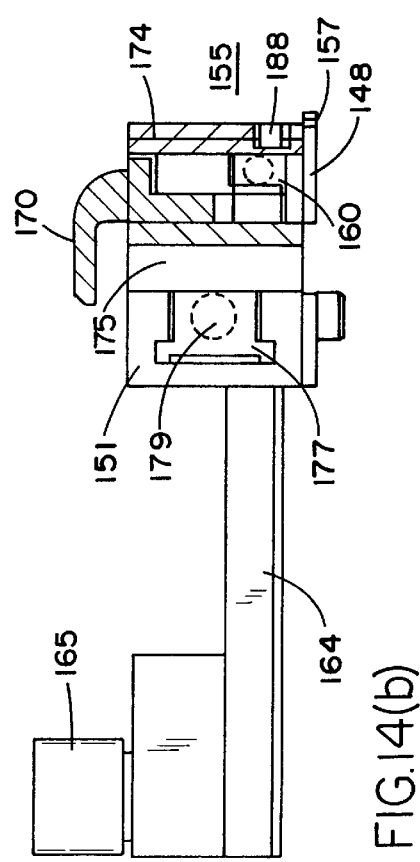

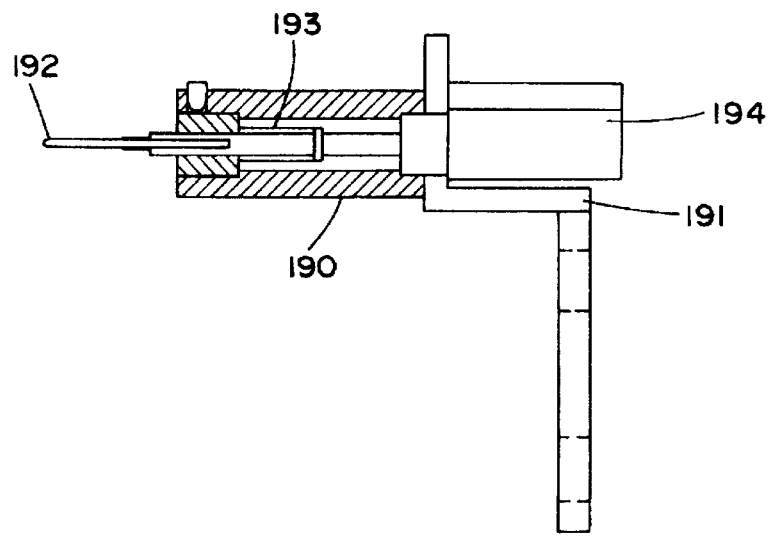
FIG.16
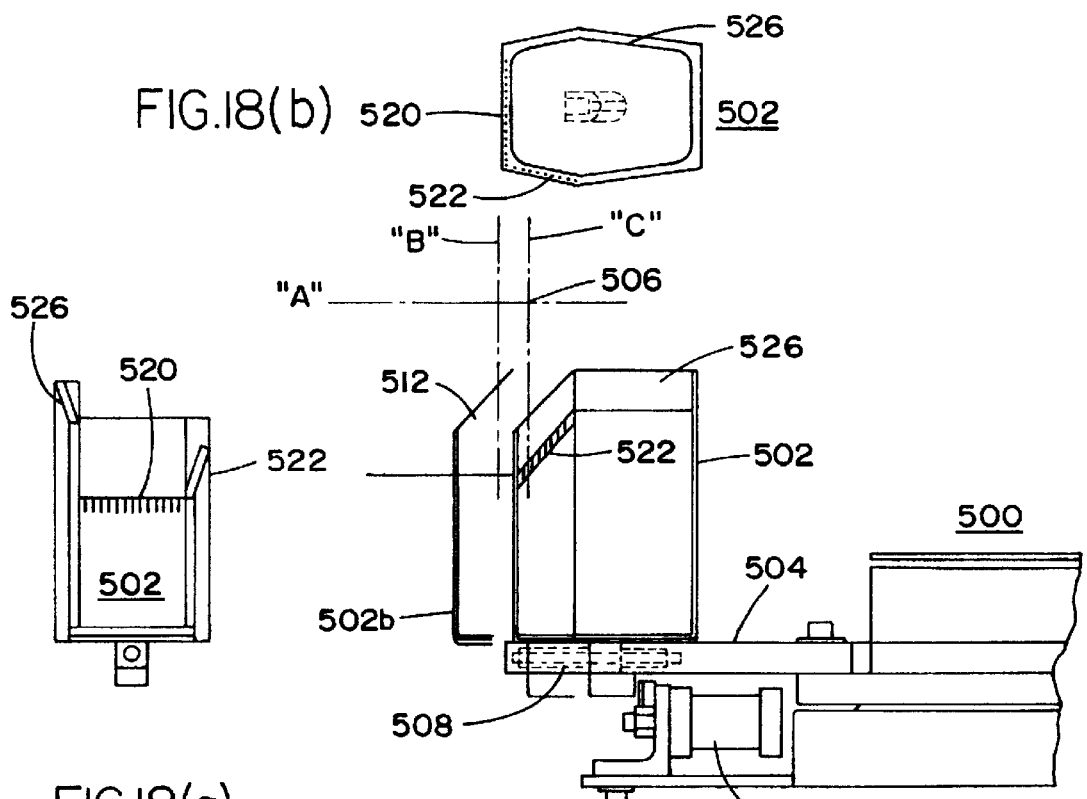
FIG.18(b)
FIG.18(a)
FIG.18

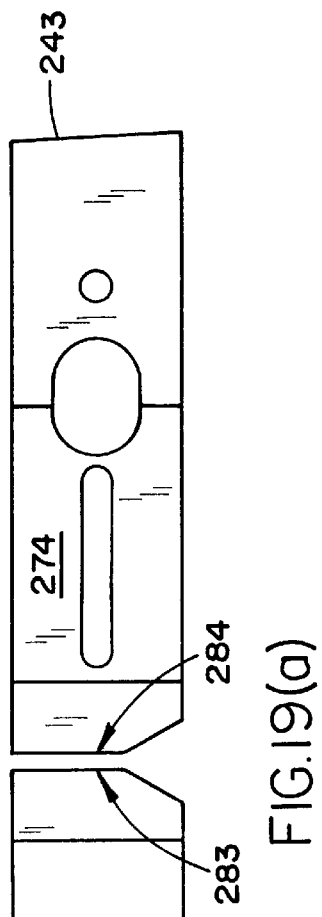
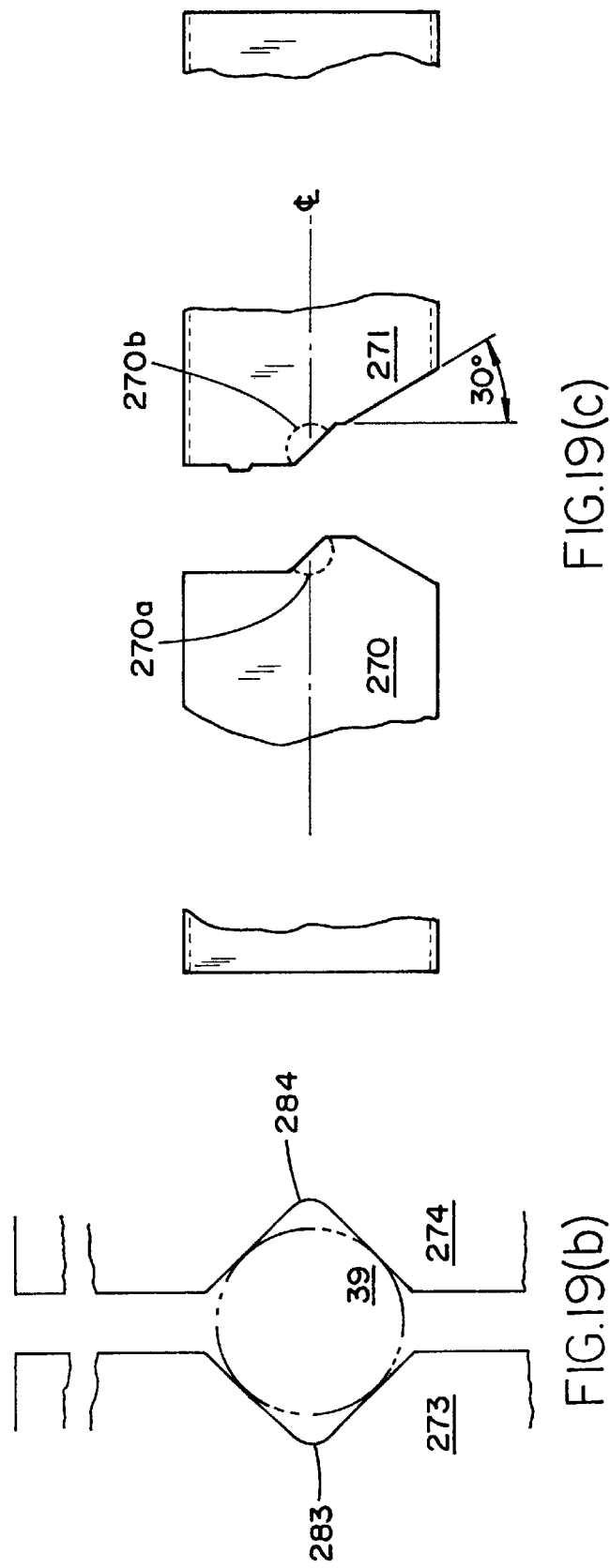
FIG.19(a)
FIG.19(b)
FIG.19(c)

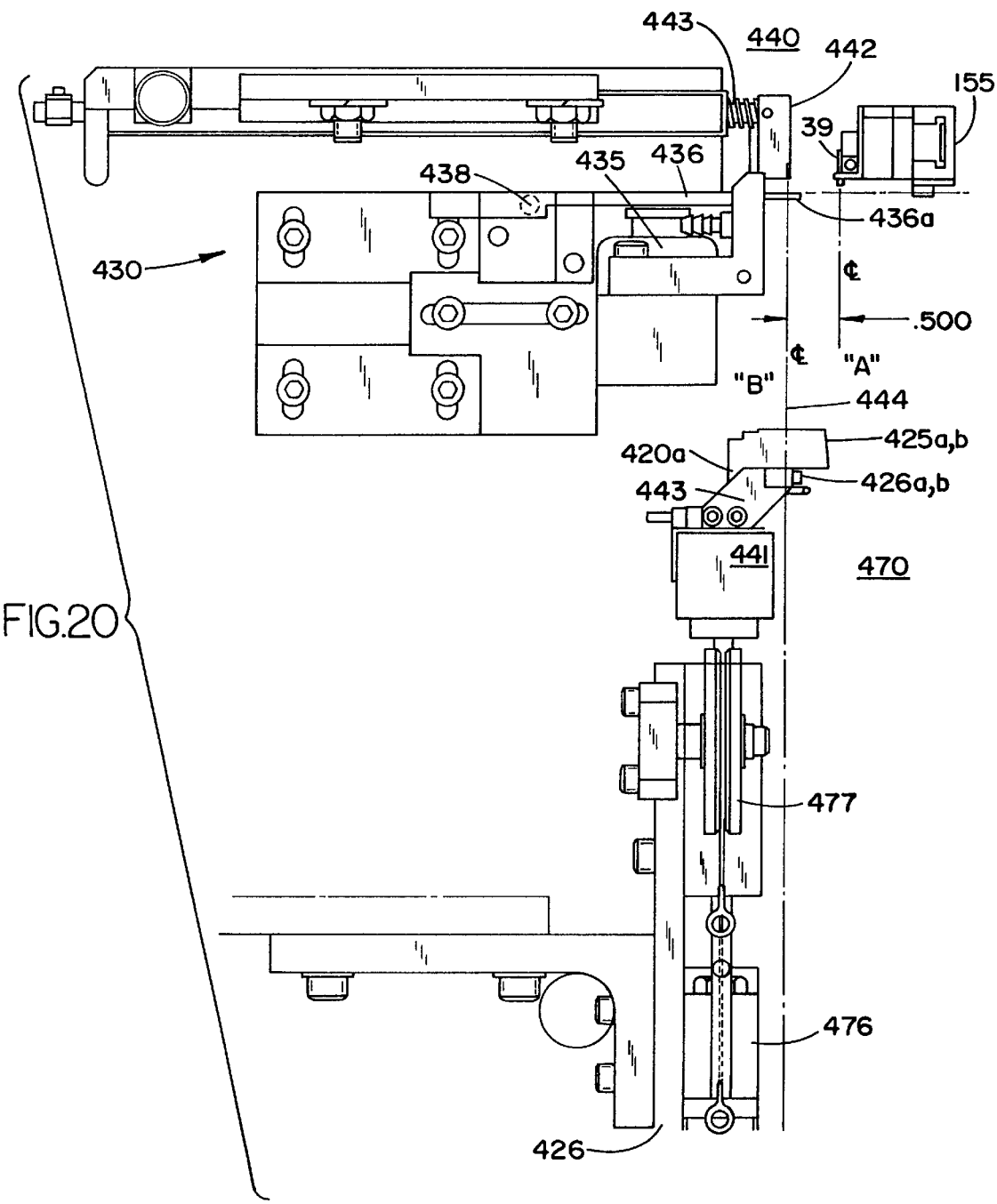

PULL TEST APPARATUS FOR PERMANENTLY ATTACHED SUTURES

FIELD OF THE INVENTION

The present invention relates generally to machines for automatically swaging needles, such as surgical needles to a suture, and more specifically, to an apparatus that automatically swages, tests, and creates bundles of armed sutures, i.e., needles having a suture strand of predetermined length attached at one end thereof, for subsequent packaging.

DESCRIPTION OF THE PRIOR ART

This application describes in detail an improvement of a portion of the pull test apparatus disclosed in a series of U.S. Patents, of which U.S. Pat. No. 5,473,810 entitled "Needle-Suture Assembly and Packaging System" and U.S. Pat. No. 5,473,854 entitled "Machine for the Automated Packaging of Needles and Attached Sutures and Method of Utilizing the Packaging Machine," are typical. All of these patents are assigned to the assignee of the present invention.

The automatic needle and suture threading machine described in U.S. Pat. Nos.5,473,810 and 5,473,854 is a highly automated machine intended for high volume production and packaging of needles and sutures wherein 20,000 to 40,000 needles and sutures are to be produced in a single run.

U.S. Pat. No. 3,980,177 in particular discusses the requirement of the surgeon or medical personnel using the armed needle to be able to detach the needle from the suture after suturing to avoid the necessity of cutting the suture with scissors. The patent itself is drawn to a needle-suture combination that is characterized as having a straight pull-out value between 3 ounces and 26 ounces depending upon the size of the suture. This patent, however, does not disclose a means for testing the armed-needle to determine its pull-out value, i.e., the means for providing the force necessary to detach the needle from the suture.

U.S. Pat. No. 4,922,904 discloses a means for confirming whether a length of suture has been firmly connected to the surgical needle or not by applying tension to the suture after swaging thereof and prior to cutting the suture. No means or method is provided for determining the amount of force that is required to separate the needle from the suture.

However, it is desirable to provide an automatic pull-test system that is designed to determine whether a needle-suture combination meets the recommended minimum pull-test requirements as set forth by the medical profession.

SUMMARY OF THE INVENTION

The present application describes an improved pull test assembly for the automatic swaging and testing of needles to sutures fed and cut to length by the apparatus, together with improvements in the operation of the apparatus.

It is an object of the instant invention to provide an automatic pull-test system that can automatically perform minimum pull-testing of the needle-suture assembly in a cost-effective manner and without manual intervention.

Furthermore, it is an object of the present invention to provide an automatic pull-test system, wherein the needle-suture assembly is automatically indexed to an automatic pull-test station after the suture has been cut and swaged to the surgical needle.

It is another object of the instant invention to provide a cost-effective automatic pull-test system that can perform a destructive pull-test of an surgical needle-suture assembly at a predetermined intervals, and moreover, that can retain the destructive pull-test values for statistical analysis thereof and statistical process control.

Still another object of the instant invention is to provide an automatic pull-test system that can perform a destructive pull-test of a needlesuture assembly and retain the maximum pull-test values thereof, and moreover, one that can provide automatic adjustment of the upstream swaging dies used to produce the armed needle in accordance with statistical process control values.

It is an object of the present invention to provided an improved pull test assembly which includes a first gripping means for use in non-destructive testing and a second gripping means for use in destructive testing of the needle-suture assembly.

The present invention is also directed to improvements for a stand alone swage machine that is particularly adapted to automated handling of the needle, automatic swaging, automatic pull testing of the combined needle and suture (armed sutures), and subsequent bundling of the armed sutures for future packaging.

It is an object of the present invention to provide a machine which will efficiently handle small batches or production runs on needles and to efficiently handle premium needles and super sharp cutting edge needles in an efficient manner without blunting the cutting edge of the needle, while bundling the same for future packaging.

It is another object of the present invention to provide a machine which is flexible in operation and enables quick changeovers between production lots and which minimizes the number of change parts required to migrate from one size needle or suture to another.

It is another object of the present invention to provide a machine which will handle odd runs or "doctors' specials" as they are referred to in the trade, where a particular surgeon expresses a preference for an unusual combination of needle type or size and suture material.

It is an objection of the present invention to provide a needle threading and swaging apparatus for attaching a suture to a surgical needle having a suture receiving opening formed therein, wherein the apparatus includes an automatic swaging apparatus which is responsive to results obtained from the pull test procedure and data to change the amount of swage pressure applied during the swage operation.

It is another object of the present invention to provide a plurality of universal grippers mounted on a swage dial for successively receiving an individual one of a plurality of precisely positioned needles at a first predetermined location and indexing each of said individual successive needles in a predetermined orientation from said first predetermined location through successive locations for sequential processing at subsequent predetermined locations, each of said universal grippers having a cam follower which cooperates with said cam dial to provide radial reciprocation of said universal grippers with respect to said swage dial in response to rotation of said cam dial.

It is another object of the present invention to provide an improved swage dial having an off set motion for the universal grippers that enables the grippers to place and retrieve needles held in a swage device having a swage die opening formed in a fixed swage die.

It is another object of the present invention to provide universal grippers which are rotated by said swage dial to each of said predetermined locations and reciprocated in and out of an operative position by said cam dial at each of said plurality of predetermined locations.

Finally, it is an object of this invention to provide a rotating array of needle collection buckets that enables collection of a predetermined number of needle and suture assemblies (armed sutures) that are bundled by the present machine for subsequent packaging in machines such as that typified by U.S. Pat. No. 5,487,212 or the machine described in U.S. Ser. No. 521,831, entitled "Single Suture Automated Packaging Machine", both of which are assigned to the assignee of the present invention.

BRIEF DESCRIPTION OF THE DRAWINGS

FIG. 9(a) is top plan view of the suture tipping assembly used in the suture drawing and cutting apparatus of the present invention illustrated in FIG. 9.

FIG. 10(a) is a top view of the swage dial assembly 150 comprising a swage dial plate 110 having four universal gripper stations 145a,b,c,d mounted thereon.

FIG. 10(b) is cross-sectional view of the four station swage dial assembly 150 showing universal gripper 155 in a retracted position.

FIG. 10(c) is cross-sectional view of the four station swage dial assembly 150 showing universal gripper 155 in an extended position.

FIG. 11(a) is detailed top view of the cam dial assembly 120 having cam dial plate 125 with cam follower 165a in a retracted position within cam track 160a.

FIG. 11(b) is cut away top view of the cam dial plate 125 showing cam follower 165a in an extended position within cam track 160a.

FIG. 14(a) is top plan view of the universal gripper and slide assembly used in the present invention, illustrating in dotted lines the various operating components thereof.

FIG. 14(b) is partially cross-sectioned side view of the universal gripper and slide assembly illustrated in FIG. 14(a).

FIG. 14(c) is a partially hidden front view of the universal gripper illustrated in FIG. 14(a) illustrating in dotted lines the actuating mechanism used to open the jaws of the universal gripper.

FIG. 16 is a partially cross section top view of the needle stripper assembly used in the present invention.

FIG. 18 is an elevation view of a needle bucket for the apparatus illustrating radial reciprocation of the needle bucket of the present invention.

FIG. 18(a) is a front view of the needle bucket for the apparatus illustrated in the elevation view of FIG. 18.

FIG. 18(b) is a top view of the needle bucket for the apparatus illustrated in the elevation view of FIG. 18.

FIG. 19(a) is a top plan view of the fixed and moveable swage dies of the present invention.

FIG. 19(b) is an enlarged view of a portion of the apparatus illustrated in FIG. 19(a) with a needle positioned therein before swaging.

FIG. 19(c) is a top plan view of portions of the suture guides of the present invention.

FIG. 20 is a diagrammatic side elevation view of the pull test apparatus of the present invention illustrating a load-cell assembly, the gripper assembly and a pull test assembly, and their relationship to the universal gripper.

DETAILED DESCRIPTION OF THE PREFERRED EMBODIMENT

The present invention is directed to improvements in a stand alone swage machine that is particularly adapted to assist in the semi-automated singulation of surgical needles to enable subsequent automated handling of the needle, automatic swaging, automatic pull testing of the combined needle and suture, and bundling for future packaging.

The present application describes improvements in the pull test and swaging assembly that swages needles to sutures, together with improvements in the operation of the apparatus.

The present invention describes an improved load cell assembly, an improved gripper assembly and an improved slide block assembly having an adjustable spring constant for non-destructive testing of the swage bond between needles and sutures.

This application describes in detail an improvement of a portion of the apparatus disclosed in U.S. Pat. No. 5,473,810 entitled "Needle-Suture Assembly and Packaging System" and U.S. Pat. No. 5,473,854 entitled "Machine for the Automated Packaging of Needles and Attached Sutures and Method of Utilizing the Packaging Machine," both assigned to the assignee of the present invention. The present invention includes an improved pull test grippers and an improved tension loading for non-destructive pull tests of the armed sutures.

The automatic needle and suture threading machine described in U.S. Pat. No. 5,473,810 is a highly automated machine intended for high volume production and packaging of needles and sutures wherein 20,000 to 40,000 needles and sutures are to be produced in a single run.

The machine described in this application is designed to efficiently handle small batches or production runs on needles and to efficiently handle premium needles and super sharp cutting edge needles in an efficient manner. It is intended to provide flexibility in operation and a quick changeover between production lots and to minimize the number of change parts required to migrate from one size needle or suture to another.

The present invention is also intended to handle odd runs or "doctors' specials" as referred to in the trade, where a particular surgeon expresses a preference for an unusual combination of needle type or size and suture material.

Needle and suture assemblies (armed sutures) are swaged by the present machine for subsequent packaging in machines such as that typified by U.S. Pat. No. 5,487,212 or the machine described in U.S. Ser. No. 521,831, entitled Single Suture Automated Packaging Machine, both of which are assigned to the assignee of the present invention.

Figure 2:
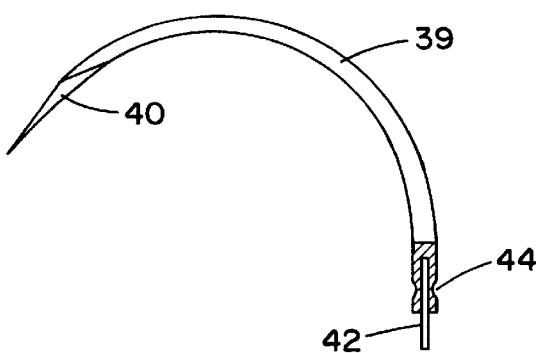
FIG. 2 is a diagrammatic view of an edged needle that is typical of the needles to be singulated and swaged according to the present invention.

As illustrated in FIG. 2, the needle 39 includes a ground or cutting edge portion 40 and is illustrated with an attached suture 42 which has been attached by swaging as indicated at 44. The suture 42 may be of any predefined length, but is commonly provided in lengths that are multiples of nine inches (18, 27 and 36 inch suture sizes are particularly common).

Figure 1:
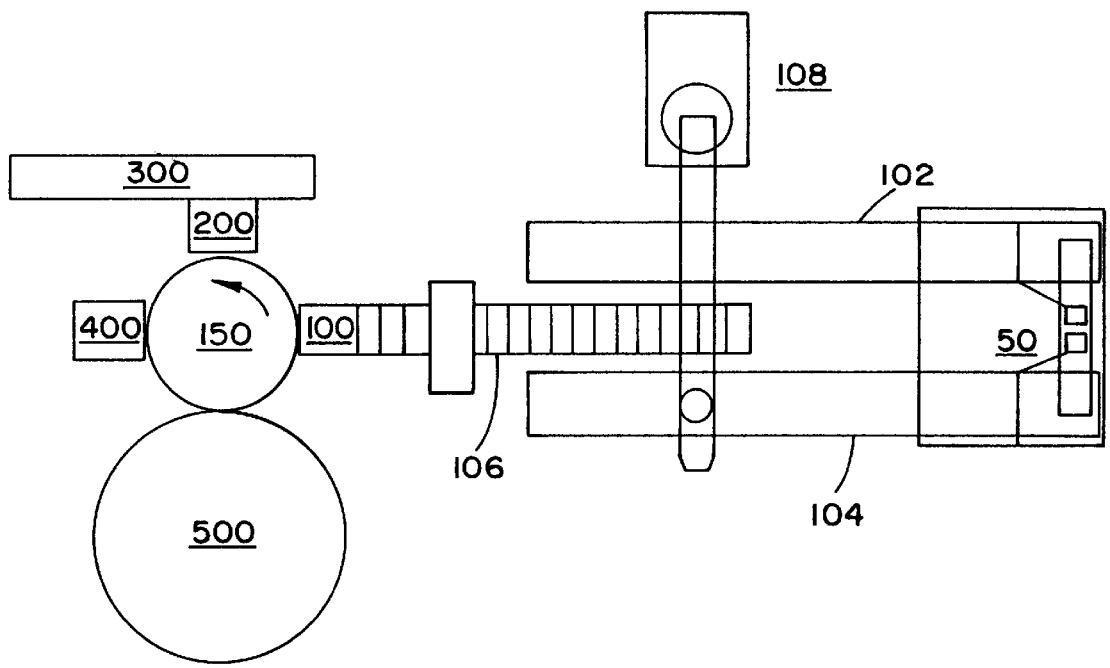
FIG. 1 is a diagrammatic top view of the needle threading and swaging system incorporating a semi-automatic needle sorting and singulating table for feeding individual needles to a universal gripper mounted on a rotary swage dial, an automatic swaging station, an automatic pull-test station, and an armed suture off-load and bundling station.

Generally, in the needle threading and swaging system of the present invention, parallel operations take place simultaneously at a plurality of different stations to ensure that approximately forty to sixty (40–60) armed surgical needles are assembled and discharged per minute. For instance, as shown in FIG. 1, a semi-automatic needle sorting and singulating station 50 assists an operator in sorting and singulating individual needles to a pair of translucent indexing conveyors 102,104 where the singulated needles are imaged by a vision system, selected by a computer, and transferred from the translucent indexing conveyors 102,104 to a precision indexing conveyor 106 by a robotic gripper 108. The precision indexing conveyor conveys precisely oriented surgical needles to a precise positioning station 100 to be sequentially received by a plurality of grippers mounted on the rotary swage dial 150. The rotary swage dial then rotates counter-clockwise as shown by the arrow in FIG. 1, to index each needle to the automatic swaging station 200 where the suture material is cut, inserted into the needle, and automatically swaged thereto. A suture drawing and cutting station 300 pulls, tips, cuts and inserts the suture into the needle to be swaged. The needle is swaged and then, the rotary swage dial 150 rotates to index the armed suture to the automatic pull-test station 400 where each armed needle is pull-tested to ensure that the minimum and/or destructive pull-test requirements of the medical profession, are met. Finally, the rotary swage dial indexes the pull-tested armed needle to the off-load station 500 where the surgical needle and suture assemblies are handed off for suture bundling for subsequent packaging at another location.

Figure 3A:
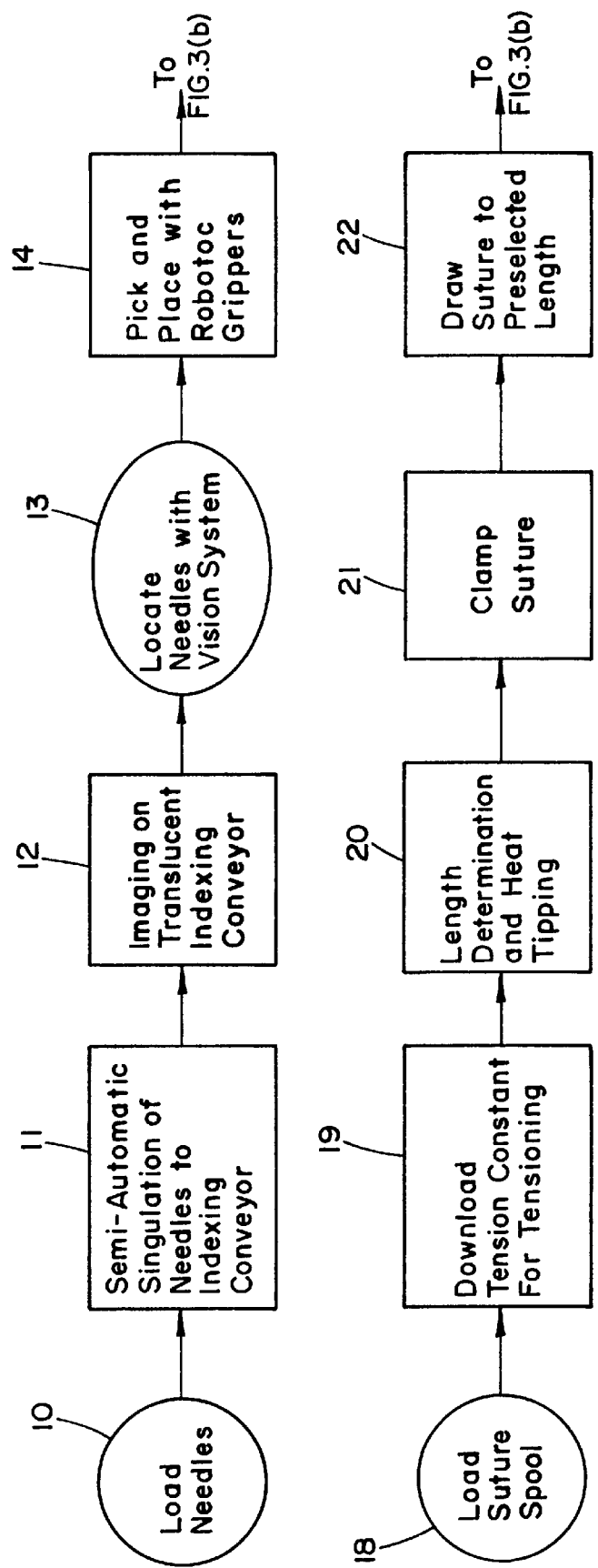
FIGS. 3(a)–3(c) together form a flow diagram illustrating the process for the needle threading and swaging system of the present invention.
Figure 3B:
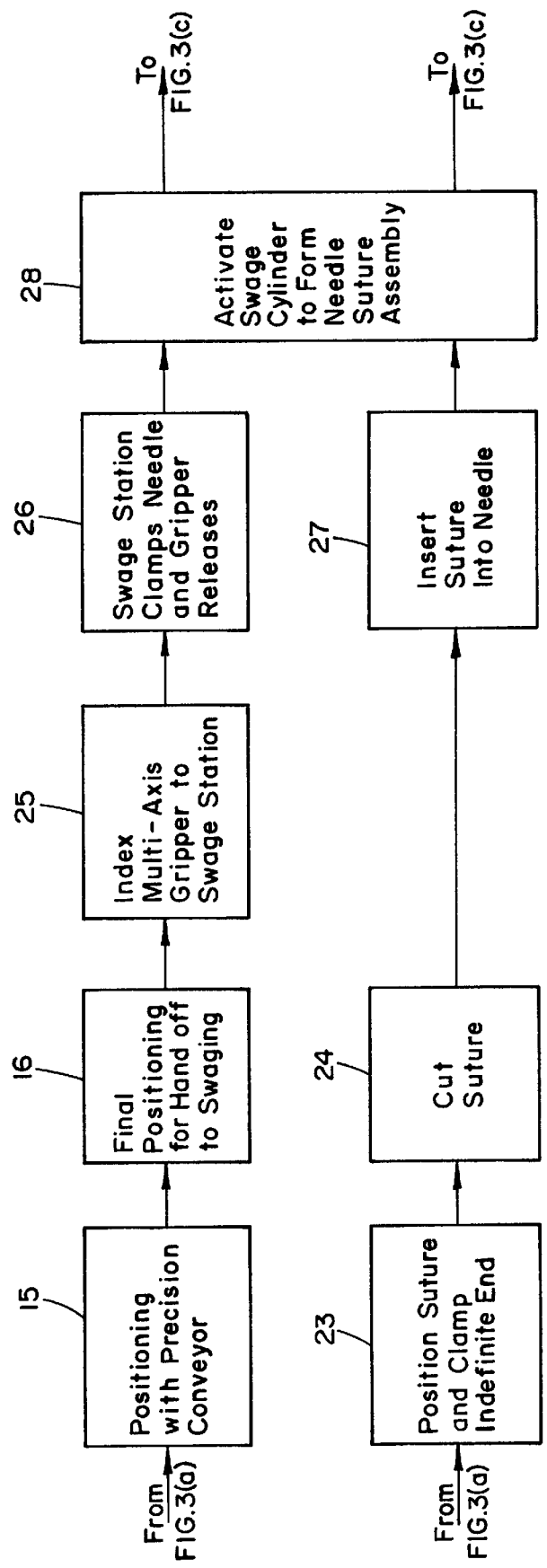
Figure 3C:
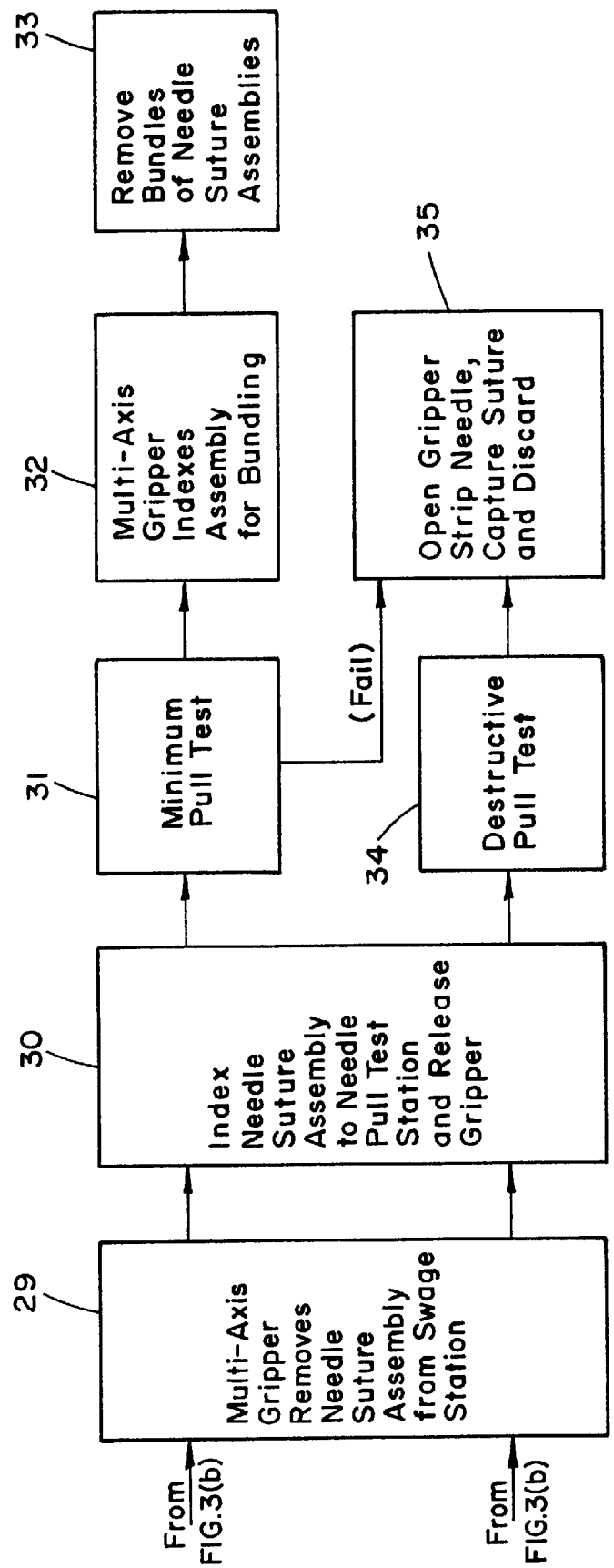

FIGS. 3(a)–3(c) are block diagrams which illustrate the automatic needle threading and swaging process of the instant invention. For instance, at the needle singulating station 50, needles are first loaded onto a flat operator work surface at 10, singulated by the operator, and then automatically and individually fed at step 11 to one of the translucent indexing conveyors 102,104. The needles; are imaged at step 12 and then evaluated with respect to orientation and position by a vision tracking system at step 13, picked up by a robot apparatus at step 14, transferred to a precision conveyor 106 for positioning by the robot apparatus 108 at step 15, and finally conveyed to a load station 100 where the needles are precisely positioned at step 16 and transferred to a universal gripper located on a rotary swage dial 150 for subsequent transfer to the swaging station 200 indicated at step 25. A detailed explanation of the apparatus used to carry out each step will be explained in further detail hereinbelow.

Simultaneous with the needle sorting process described above with respect to steps 10 through 25, an automatic suture cutting process takes place at the suture station 300 as shown in FIGS. 3(a) and 3(b) with respect to steps 18 through 28. Indefinite length suture material is supplied in various spools and configurations that may carry up to 5000 yards of material. This is indicated at step 18 in FIG. 3(a), where the suture material is loaded into a payoff assembly. A tension constant for the suture to be drawn is downloaded as indicated at step 19. A drawing tower apparatus includes grippers that alternately draw lengths of the suture material from the spool to enable cutting thereof which lengths are predetermined at step 20.

While the material is being drawn, it may require extra treatment or processing. For instance, as described in detail below, it may be desirable to heat the suture material under tension at the area which will become the suture tip in order to stiffen the material to facilitate the positioning thereof within the suture receiving opening of a surgical needle. Thus, at step 20, heat may be applied to a portion of suture material. In the preferred embodiment of the invention the heating step is performed upstream of the drawing and cutting apparatus to enable the suture to partially cool and harden before cutting. At step 21 of the block diagram of FIG. 3(a), the suture material is clamped and gripped by the servo grippers, and at step 22, the suture strand is drawn to a predetermined length and positioned for insertion within the suture receiving opening of the needle for swaging.

Referring now to FIG. 3(b), as the suture is positioned for insertion, a second suture clamps the suture at a position which will hold the indefinite length end at step 23, and the suture is cut at step 24 to separate the suture of predetermined length from the indefinite length suture.

After a surgical needle is indexed to the swaging station 200 as described above, the universal gripper positions the needle in a precisely oriented position at the swage die opening formed at the ends of two swaging dies of a swage assembly as indicated as step 26 in FIG. 3(b). Simultaneously, the suture strand is drawn along a suture axis to register a tip thereof for insertion within the suture receiving end of the needle. Next, at step 27, the gripper assembly at the drawing tower inserts the tip of the suture strand within a lower funnel guide for accurate positioning within the suture receiving opening of the needle that is aligned with the suture drawing axis. At step 28, the swage cylinder is activated to automatically swage the suture to the needle. Referring now to FIG. 3(c), the universal gripper is actuated to grip the needle, and then retracted on the rotary swage dial as shown as step 29 and indexed to a pull-test station 400 at step 30 so that minimum pull-testing at step 32 or destructive pull-testing at step 34 may be performed.

Depending upon the results of the minimum pull-test, the needle and suture assembly will either be indexed by the rotary swage dial to the off-load station 500 where the armed needle will be bundled if the pull-test requirements are met (as shown as step 32 in FIG. 3(c)), or, will be discharged at the pull-test station if the needle fails the minimum pull-test (as shown as step 35 in FIG. 3(c)). The destructive pull-test always renders the needle incapable of further processing so the needle is automatically discharged at the pull-test station 400 as indicated at step 35 in FIG. 3(c). Finally, as shown as step 33 in FIG. 3(c), needle and suture assemblies passing the minimum pull test are conveyed to an off-load station 500 where the individual armed sutures are bundled for subsequent packaging and sterilization.

A detailed explanation of the apparatus used to carry out each step in the suture cutting process will be explained in further detail hereinbelow.

Overview of the Apparatus

Figure 4:
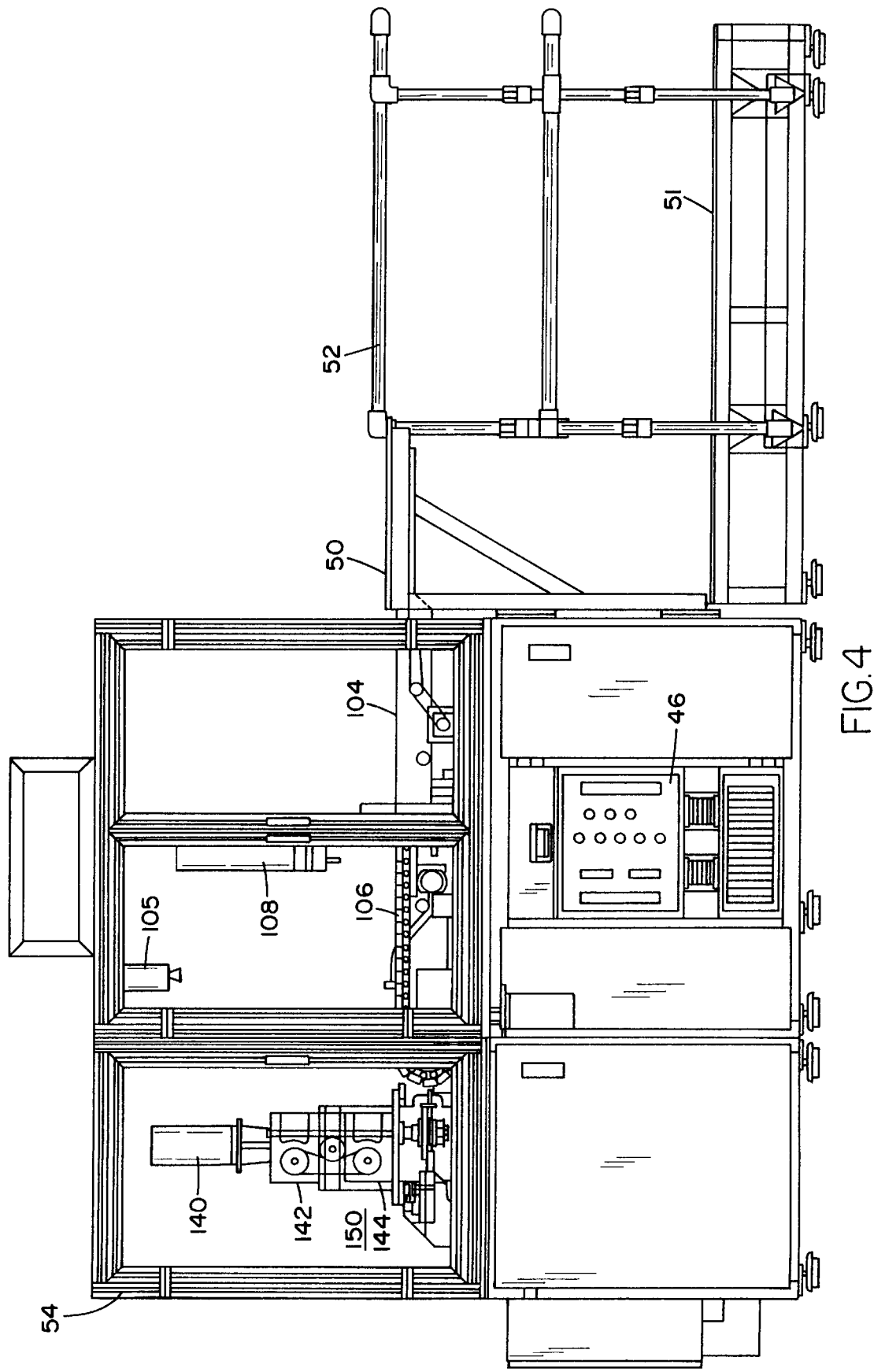
FIG. 4 is an elevation side view of the present invention illustrating an operator station, a control computer, portions of the robotic handling device, and the swage drive of the present invention.
Figure 5:
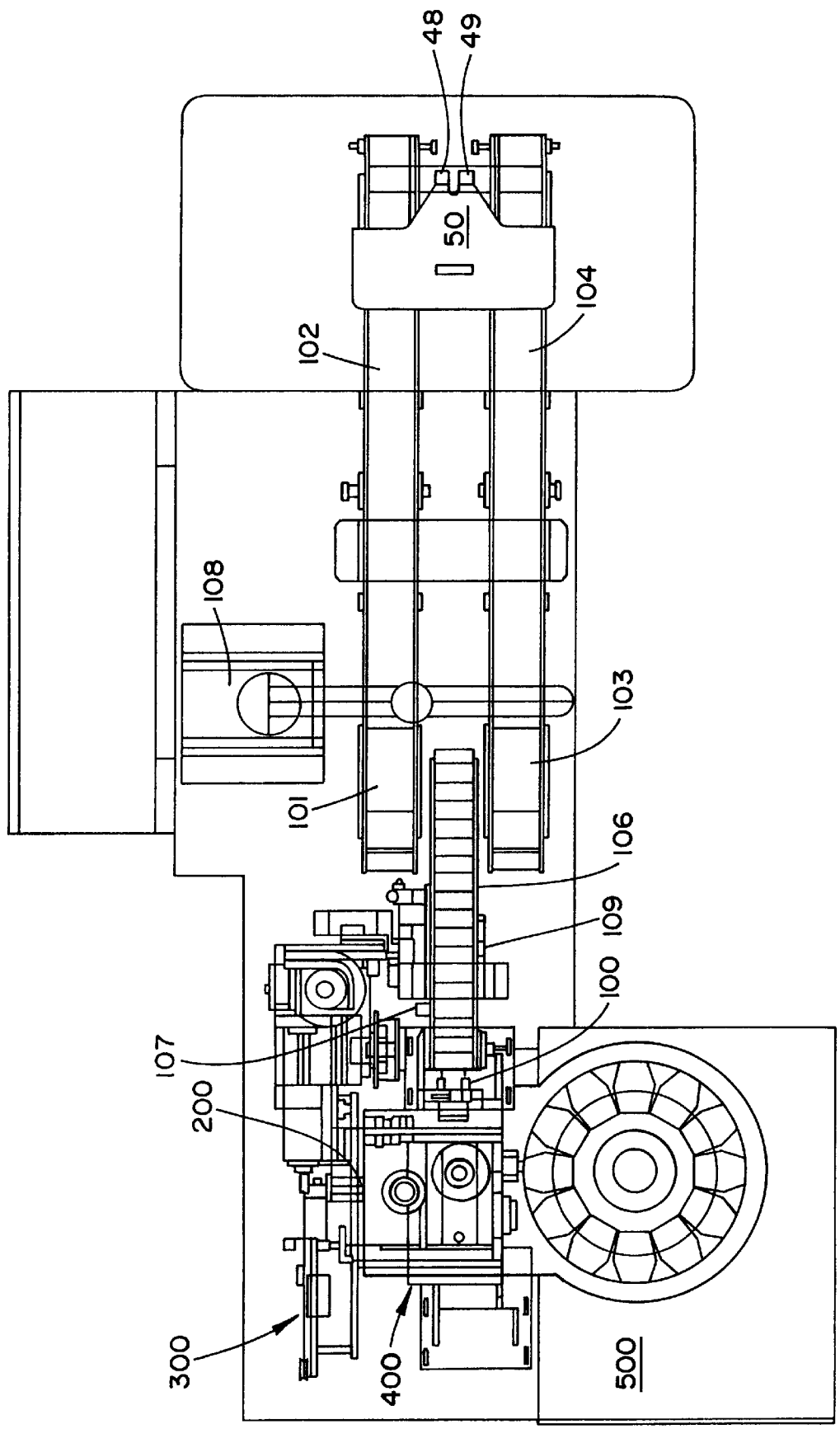
FIG. 5 is a top plan view of the present invention with the operator safety guards illustrated in FIG. 4 removed.
Figure 6:
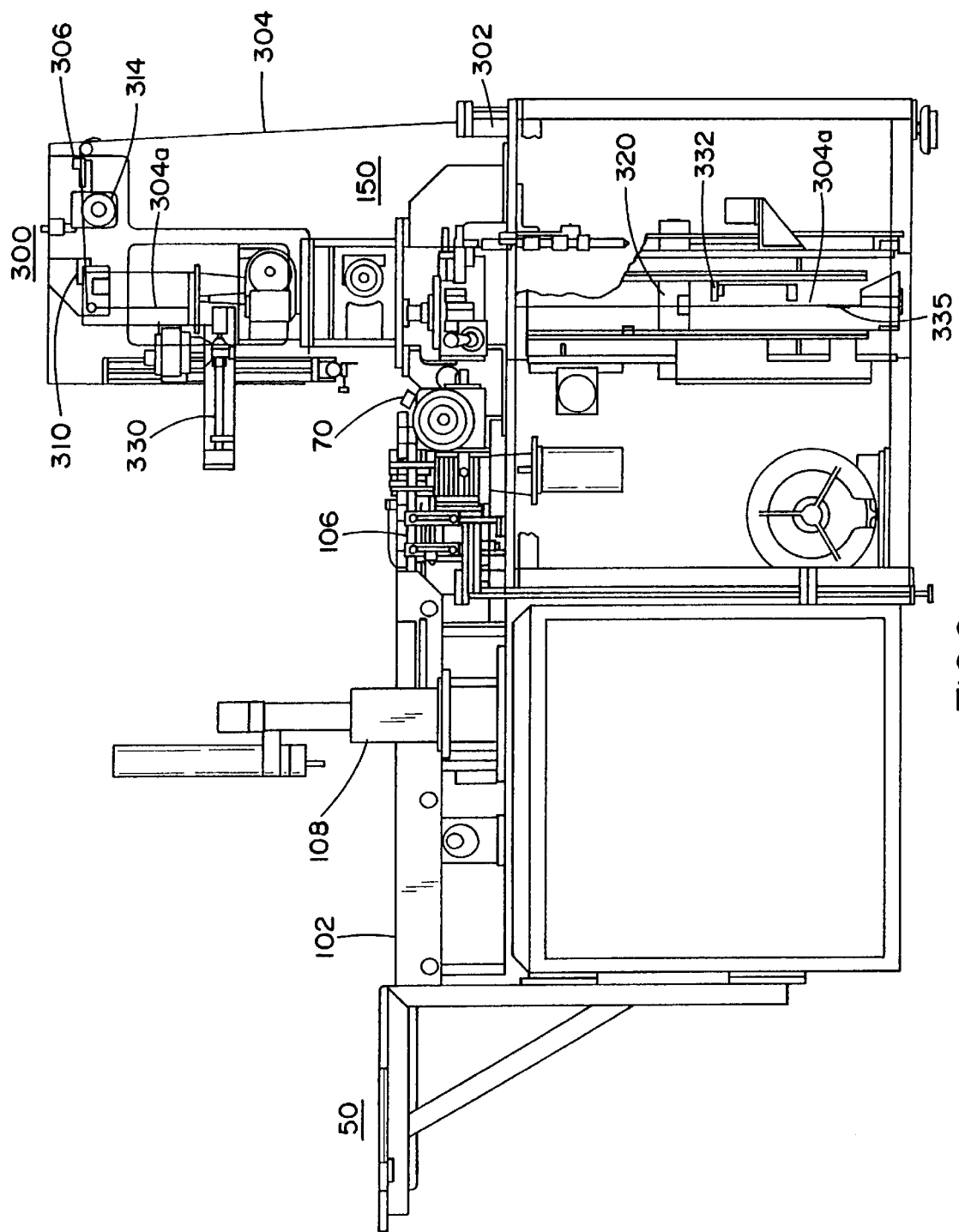
FIG. 6 is a detailed elevation side view of the present invention from the opposite side as illustrated in FIG. 4, with the operator safety guards removed.

FIG. 4 is an elevation view of one side of an apparatus constructed according to the teachings of the present invention, and FIG. 5 is a top plan view of the apparatus with the safety guards removed. FIG. 6 illustrates the apparatus from the opposite side as FIG. 4. FIGS. 4–6 are used in the following descriptive overview of the apparatus. This apparatus includes a singulation area or table 50 to assist: an operator in singulating needles that are deposited to the translucent conveyors 102,104, one of the conveyors 104, being depicted in FIG. 4. The operator work station includes a platform 51 for operator seating and guard rails 52 for operator safety. Safety guards 54 are also provided around the machine for safety purposes.

Each of the needles singulated by the operator are dropped through openings 48,49 by sliding the needle along the table surface 50. This step avoids the needle to needle contact inherent in the vibratory feed bowls illustrated in U.S. Pat. No. 5,473,810 and thus substantially reduces the risk that premium needles or cutting edge needles will be blunted by needle contact. As each needle is dropped, it lands at an intermediate staging location, and at an appropriate interval, after each index of the indexing conveyor, the needles is blown by a puff of air to the translucent indexing conveyor, with needles dropped through opening 48 being transferred to translucent indexing conveyor 102 and needles being dropped through opening 49 being transferred to translucent indexing conveyor 104.

The needles thus transferred are indexed forward to imaging stations 101,103 wherein a back light provides a high contrast image of the needle against a white background for imaging purposes. The indexing conveyors 102, 104 are indexed approximately 2 inches at each index. By limiting the incremental advancement the image processing is step is enhanced, and problems associated with inertial loads on the needles on conveyors 102,104 are minimized. If the indexing conveyors 102,104 are accelerated too quickly, the needle will remain in its drop position and not be advanced forward, and conversely, if the needle is moving on the conveyor, and the conveyor is stopped too quickly, the needle will continue to travel after the conveyor is stopped. The present apparatus seeks to avoid either of these situations by minimizing the amount of index at each incremental step while still providing enough movement to provide an adequate supply of needles to the apparatus.

The needle singulating apparatus illustrated provides a single needle at each drop point which substantially enhances the accuracy of the vision system and minimizes needle returns that might otherwise be necessary for overlapping or nested needles that were either not imaged, or selected by the computer control means 39 for transfer by the robotic apparatus 108.

The needles deposited on the translucent indexing conveyor 104 are imaged by a vision system 105 and these images are processed by a computer control means 46 to identify the orientation and X,Y coordinate location of the needles. Determining the X,Y coordinates alone is not enough in the needle swaging environment inasmuch as the robotic apparatus needs to determine, in the case of a symmetrically formed curved needle, which end is the barrel end and which end is the cutting end in order to properly place the needle for subsequent automated handling. After both the orientation and location have been determined, a robotic apparatus 108 picks the needles from the translucent conveyors 102,104 and places them on a precision indexing conveyor 106. The precision conveyor 106 includes a plurality of "boats" 70 which are particularly adapted to provide precision positioning of the needle. The rotary swage dial 150 includes a drive motor 140 and first and second indexing transmissions 142,144 which are used to drive the swage dial in a manner as will be hereinafter explained in detail.

The needles transferred by the robotic apparatus 108 are transferred so that the butt end of the needle 44 is engaged by gripping jaws on the conveyor boats 70 of the precision conveyor 106. While the butt end is located and gripped by the robotic apparatus 108, at the point of pickup it may be oriented in either direction of curvature. For particularly small needles a fixed post may be provided for the robotic apparatus to use in correcting the orientation of curvature. For larger needles, a needle plow 109 is used so that the direction of curvature for each of the needles is uniform. As illustrated in FIG. 5, the apparatus also includes a prepositioner 107 which is adapted to approximately locate the butt end of the needle and an adjustable hard stop assembly at station 100 that precisely registers the butt end of the needle to an accuracy of 0.001 inches.

The needle singulation apparatus, and the operation of the indexing conveyors 102,104, the robotic apparatus 108 and the precision conveyor 106 is more fully described and claimed in U.S. Ser. No. 08/847,133, attorney docket 10183, entitled "Semi-Automated Needle Feed Method and Apparatus," the disclosure of which is incorporated herein by reference thereto.

After the needle has been received at the precise positioning station 100, it is gripped by one of the universal grippers located on the swage dial mechanism 150 to be indexed through a plurality of stations including a swage station 200 wherein a suture of definite length is cut from a suture spool of indefinite length at station 300 and inserted into the needle at swage station 200 for permanent assembly thereto. After swaging, the needle is advanced to the pull-test station 400 for testing of the needle suture bond, and then indexed to a bundling station 500 wherein a plurality of buckets are circumferentially arranged on a rotating turntable to receive a predefined number of needles and sutures in each bundle.

Figure 13:
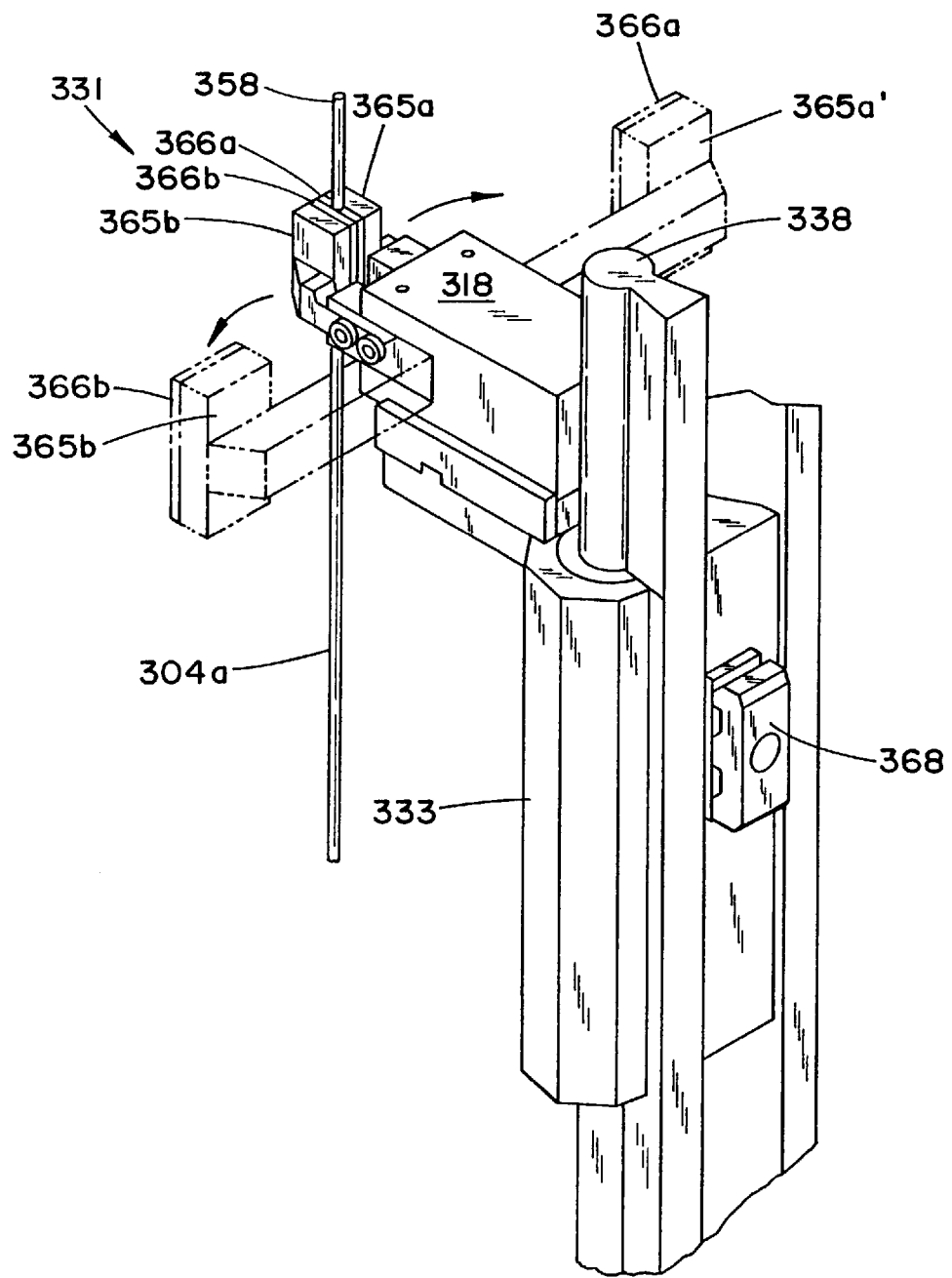
FIG. 13 is an enlarged isometric view of a suture gripper assembly having gripper arms shown in their open (dotted lines) and closed (suture gripping) positions.

FIG. 6 illustrates the apparatus of the present invention from the opposite side of the machine illustrated in FIG. 4 and includes breakaway portions to more particularly illustrate portions of the precision conveyor apparatus and the suture drawing and cutting station 300. As illustrated in FIG. 6, a spool of suture material 302 is mounted on a convenient location and the indefinite length suture material 304 is fed to the suture drawing station through a pretensioning apparatus 306, a tensioning roller 314 having a computer controlled tension constant which may be selectively downloaded from the computer control means 46 to match the suture material 304 being handled, and a knot detector 310 which may be used to provide a knot presence signal to the control computer 46 to reject that length of suture after swaging to a needle. From the knot detector 310 the suture strand 304a is fed through a tipping station 330 which heats the suture strand to a predetermined temperature to assist in tipping and cutting the suture for insertion into the surgical needle. From the heating and tipping station 330, the suture material is passed to the bottom of the machine to a turnaround roller 335 where it is grasped by first and second suture clamps which advance the suture material 304a in a hand over hand manner. As illustrated in FIG. 13, clamp 331 includes a traveling carriage 333 which reciprocates up and down frame member 338 by means of a timing belt which is secured to the carriage at 368. A pneumatic actuator 318 includes first and second clamps 365a,365b and first and second gripping surfaces 366a,366b which clamp the suture material therebetween.

In a first cycle of operation, clamp 331 draws the suture of indefinite length to a suture insertion point immediately adjacent the swage plates of the swaging station and then dwells while a second suture clamp clamps the indefinite suture length below the suture cutter 334 (illustrated in FIG. 9). After the second suture clamp has engaged the suture, the cutter 334 is actuated to cut the suture and the tip end of the suture 358, illustrated in FIG. 13 is inserted into the needle as illustrated in FIG. 15(b). The tip end of the suture 358 is positioned below a funnel dye formed in suture alignment plates 270,271 which reciprocate immediately below swage plates 273,374. After the suture tip end 358 has been inserted into the barrel end 44 of needle 39, the swage station is actuated driving the swage plate 273 against swage plate 274 to swage the suture tip 358 in the surgical needle 39.

Suture Drawing and Cutting

Figure 9:
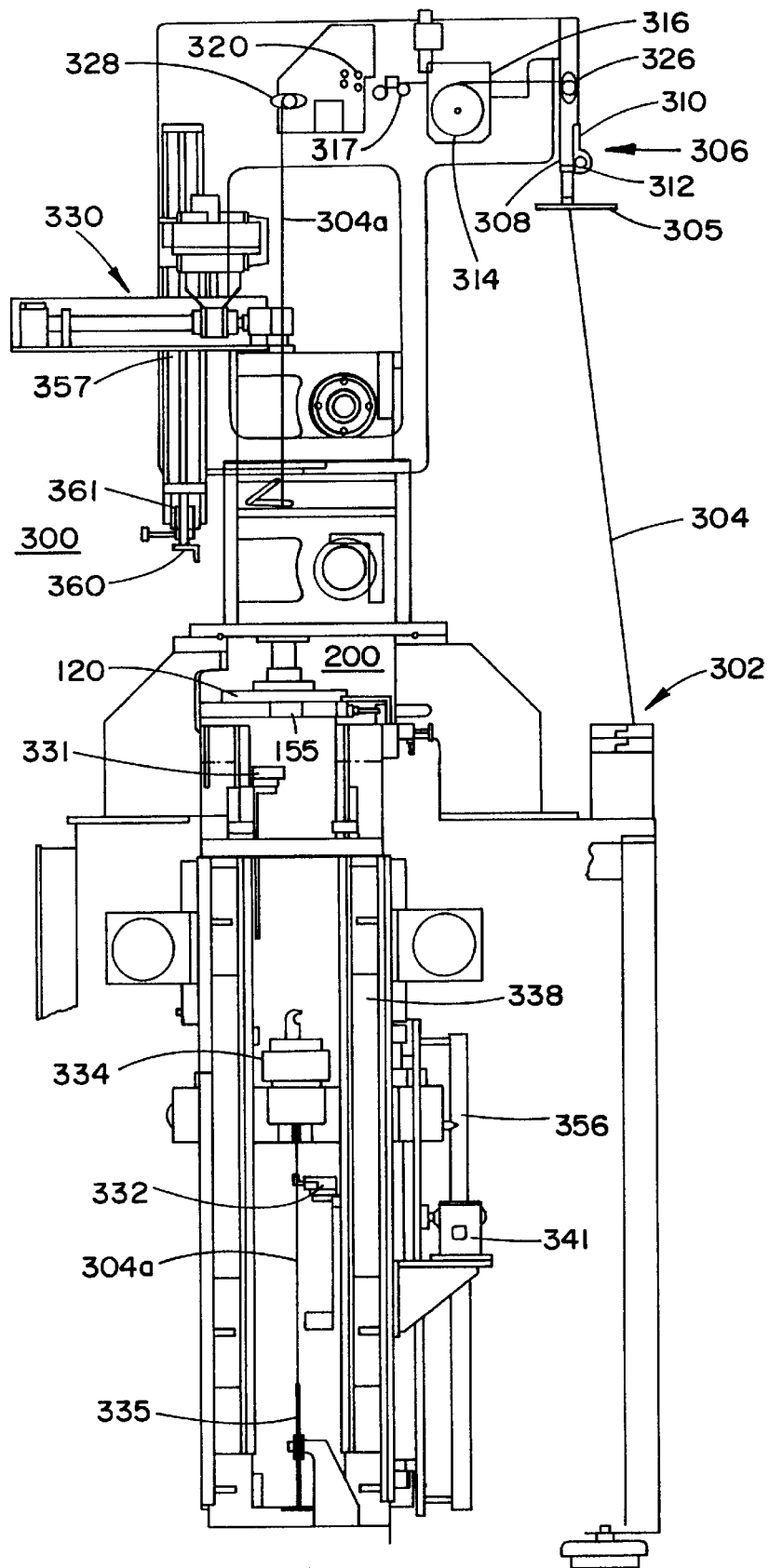
FIG. 9 is front elevation view of the suture drawing and cutting tower assembly used in the present invention.

FIG. 9 illustrates a front elevational view of one designed embodiment of a servo tower 300, similar to that shown in FIGS. 2–6, and shows the suture path therethrough. Suture 304 is pulled off one end of a supply roll 302 mounted to one side of the servo tower, through the center of an annular guide disc 305, and into a mechanical tensioner 306. The mechanical tensioner can comprise a stationary guide frame 308 and a pivotally mounted guide frame 310, pivotally mounted about a pin 312 at the lower end of the stationary guide frame. Each of the stationary guide frame and the pivotally mounted guide frame has a series of spaced guide elements, each with a central guide aperture therein, which are alternately interleaved, such that the spaced guide elements of the pivotally mounted guide frame alternate with the spaced guide elements of the stationary guide frame. The pivotally mounted guide frame 310 is spring biased about the mounting pin 312 to rotate the top thereof away from the top of the stationary guide frame, such that the suture extending between the alternating stationary guide frame elements and the pivoted guide frame elements is placed under tension while being pulled therethrough.

The suture then travels over idler roller 326, and extends to and is wrapped twice around a tension roller 314 which is mounted on one end of a torque motor 316, (illustrated in dotted lines in FIG. 9) which applies a given tension to the suture as it is pulled through the servo tower by the first and second gripper assemblies 331, 332. The gripping assemblies alternate in a hand over hand advancement as previously described in U.S. Ser. No. 08/181,595, entitled "Suture Cutting System," the disclosure of which is incorporated herein by reference thereto. Each different suture size and material should have a different tension applied thereto as it is drawn through the apparatus. The torque motor 316 provides a different tension force for each different suture size and type, and the specific tension force(in grams per volt to be applied by the torque motor) is downloaded from a computer program at each suture batch changeover. The proper tension is important for several operations described herein, and is particularly important for the cutter assembly to operate while providing a clean neat cut without a broom effect.

The suture then extends to an out-of-suture sensor positioned at 317, and then through a knot detector 320. The suture 304 then travels to a second idler roller 328 to change direction again, from which the suture 304 extends vertically downwardly through a heated tipping assembly 330, which heats and ultimately stiffens a small length of the suture, at which small length the suture is subsequently cut and the cut tip is inserted into and swaged to a needle.

The suture 304 then extends downwardly from the tipping assembly to a large idler roller 335 mounted near the bottom of the machine having an appropriately 7 inch diameter, at which the suture reverses direction and travels vertically upwardly to the first and second gripper assemblies 331, 332, to the suture cutter assembly 334 and a suture swaging During the insertion operation, the cut suture end is guided by a funnel shaped aperture 270(a),271(a) in a suture guides 270,271 into the aperture in the end of a needle, after which a moving anvil 273 is moved relative to a stationary anvil 274, of a swage die, to swage and attach the needle to the suture.

In this embodiment, after initialization, one gripper assembly will be in a home position, 2" below the face of the swage die mounting surface, allowing a 2.03" movement from the home position to an insert position. A proximity switch is located on each tower at 2" below the face of the swage die mounting surface to set the home position during an initialization procedure.

Assuming that the machine is being initially set up to cut a desired length of suture, the cutter assembly 334 will be moved to a predetermined vertical position in the swaging machine by operation of the handcrank attached to gearbox 341. This is done by aligning a pointer for the cutter assembly with a vertical scale 356 positioned on the side of the swaging machine, similar to the vertical scale 357 shown above for the tipping assembly.

The cutter assembly includes a proximity switch thereon, and during an initialization procedure, the position of a gripper assembly is detected by the proximity switch, and that position is set in memory to set the servo gripper bottom position 332 during subsequent normal operation of the machine. The tipping assembly is also moved to an appropriate position in the machine as described hereinbelow.

FIG. 9 shows the right gripper 332 positioned slightly below the cutter assembly 334 so that the indefinite length strand will be gripped when the definite length swaged strand is cut. Thus, the upper left gripper 331 now grips the suture material 304 having a tipped end 358 and it now becomes the lead (gripper. The next cycle begins with the lower gripper 332 vertically drawing the material 304 along the height of the drawing tower 300 for the long stroke to position the next strand to be cut for insertion within the surgical needle.

During this operation, assume that the upper gripper assembly 331 has just moved to its home position. At the home position, the gripper assembly 331 stops and waits a predetermined time, during which a needle is preclamped in an insertion position in the swaging station 200, and then moves to the insert position. The following operations are then performed substantially simultaneously. The bottom gripper assembly 332 closes, a tipping operation is performed simultaneously at the tipping assembly 330, and the swage station is simultaneously actuated to swage the needle end around the suture, attaching it thereto. Thereafter, the cutting assembly 334 is activated, cutting in the tipped area to cut the suture to the given length. Thereafter, the upper gripper assembly 331 opens, and the assembly 331 returns to the bottom position, and simultaneously therewith the lower gripper assembly 332 moves up to the home position, and the cycle is then repeated.

After removal of the swaged needle and attached suture length from the apparatus, it is subjected to a sterilization operation, during which the suture length incurs some shrinkage. Accordingly, the cut lengths of suture must be cut to lengths slightly longer than their desired(or label) final lengths to compensate for such shrinkage.

The following table gives, for silk suture, in the left column the commercial(or label) suture length, in the middle column the low servo position of the low gripper assembly below the face of the swage die mounting surface, and in the right column the cut length of suture prior to shrinkage. VICRYL shrinkage during sterilization is approximately 3% of the table values for silk.

| 18" | servo - 16.51 | allowed for 18.350" |
|---|---|---|
| 27" | servo - 25.51 | allowed for 27.350" |
| 30" | servo - 28.51 | allowed for 30.350" |
| 36" | servo - 34.51 | allowed for 36.350" |

As described above, after heating of a predetermined length of suture at the tipping assembly, the suture must cool to allow setting and hardening of the suture material prior to cutting of the suture at the hardened length and insertion of the cut stiffened end into a needle. This cooling of the suture is provided in this embodiment by allowing a discrete number of machine cutting cycles to occur between tipping of the suture and cutting of the suture. This is provided by allowing a predetermined long length of suture travel between the tipping assembly and the cutter assembly. Hence, the suture tipping assembly 330 is positioned near the top of the servo tower, and after heating thereat, the suture travels to the bottom of the machine, around the large idler roller 335, and then back upwardly to the cutter assembly 334. The large diameter of the idler roller 335, relative to the other idler rollers 326, 328, is provided because the small length of suture which has been heated at the tipping assembly 330, has begun to harden and set by the time the heated section reaches the large idler roller. The large diameter thereof facilitates the suture to travel therearound without picking up a permanent curved set from the large idler roller, as it is desirable for the suture to be straight, without any curve, when it is subsequently cut and inserted into a needle. The idler rollers 326 and 328 typically have a 0.5 inch diameter, whereas the large diameter roller 335 has a diameter preferably greater than 6.0 inches, approximately 7.0 inches in one embodiment.

The operation of the machine depends upon a discrete whole number of machine cutting operations to be performed between the tipping and cutting operations. Accordingly, for each different length of cut suture, the tipping assembly 330 must be positioned at a different predetermined position within the machine for the tipped section of suture to be precisely and correctly positioned at the cutter assembly 334 after a given number of machine cycles.

The following table gives in its columns, proceeding from left to right, the label suture length, the actual cut suture length, the number of machine cycles or increments provided between tipping and cutting, the total travel length of the suture between tipping and cut ting, the tipping assembly vertical position above the table top, and the tipping assembly scale pointer position above the table top (explained in greater detail hereinbelow).

| SUTURE LENGTH | | | | ABOVE TABLE TOP | |
|---|---|---|---|---|---|
| LABEL | ACTUAL | INCREMENTS | TOTAL | TIPPER C | POINTER |
| 18 IN. | 19 IN. | 6 | 114 IN. | 27.64 IN. | 25.89 IN. |
| 27 IN. | 28 IN. | 4 | 112 IN. | 25.64 IN. | 23.89 IN. |
| 30 IN. | 31 IN. | 4 | 124 IN. | 37.64 IN. | 35.89 IN. |
| 36 IN. | 36.25 IN. | 3 | 108.75 IN. | 22.39 IN. | 20.64 IN. |

Figure 9B:
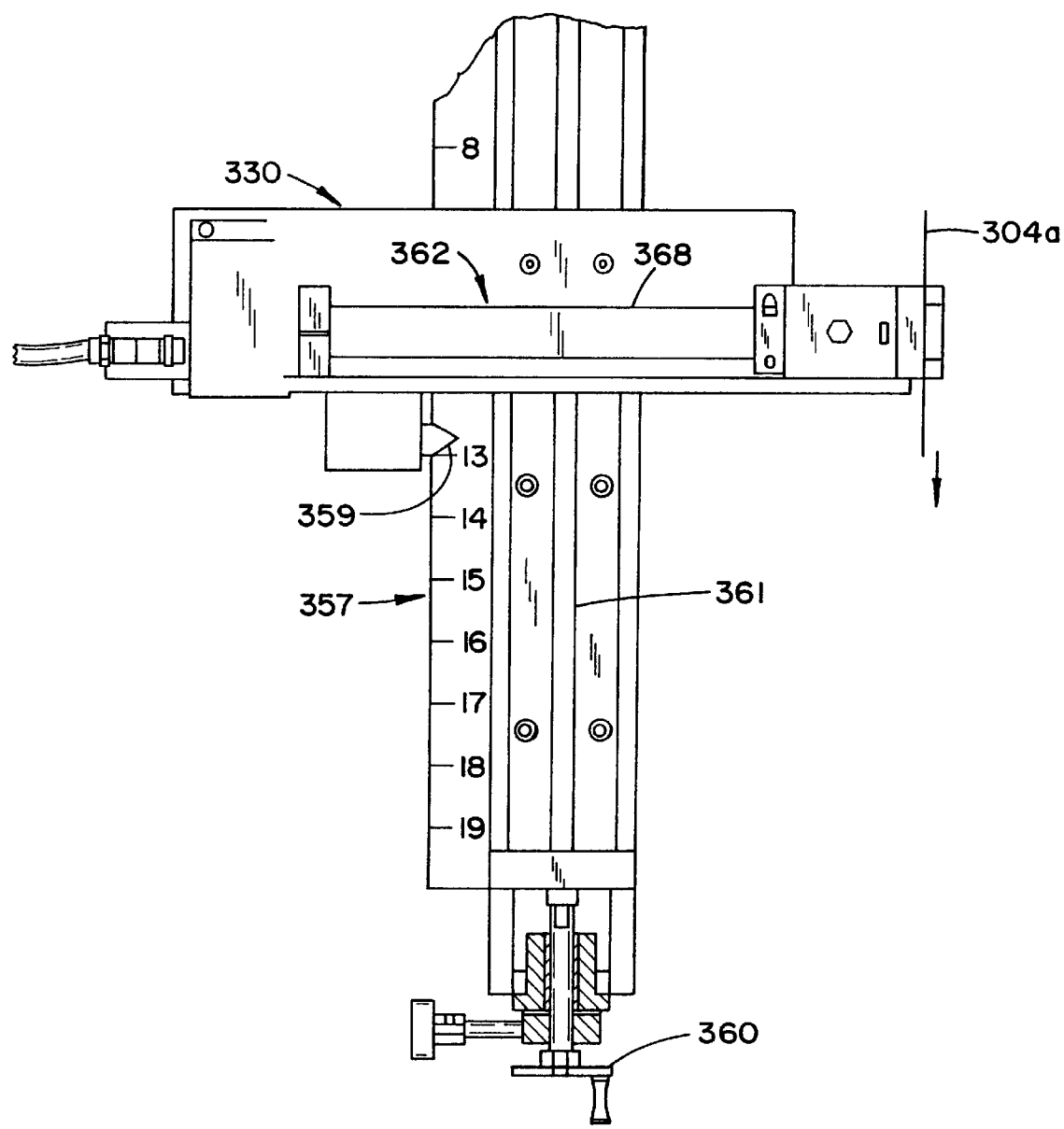
FIG. 9(b) is front elevation view of the suture tipping assembly illustrated in FIG. 9(a) and used in the suture drawing and cutting apparatus of the present invention.

FIG. 9(b) illustrates an enlarged front elevational view of the suture tipping assembly at which a small length of the suture is heated to stiffen the suture material after subsequent cooling thereof, in preparation for cutting a given length of the suture and inserting the lead cut end of the suture into the end of a needle for swaging thereto. FIG. 9(b) illustrates the movement of the tipping assembly 330 along a vertical scale 357 provided adjacent to the tipping assembly 330. The vertical position of the tipping assembly in the machine is adjustable by a handarank 360 and precision lead screw 361, similar to the positioning mechanism for the cutter assembly as described hereinabove. As the handcrank is rotated, the vertical position of the tipping assembly 330 in the machine is changed, and is precisely positioned by reading a pointer 359 attached to the tipping assembly on the scale 357. A chart is provided for the machine which gives, for each desired length of suture, the appropriate position for pointer 359 of the tipper assembly 330 on the vertical scale 357, and a similar position for the cutter mechanism 334 on the vertical scale 356.

In this embodiment, the position of the cutting mechanism along the drawing axis is continuously adjustable to provide an infinite number of possible different lengths of cut suture. For each different cutting position of the cutting mechanism, the tipping mechanism is adjustably positioned at a different predetermined position in the apparatus to provide for the tipped section of suture to be precisely positioned at the cutter mechanism for a discrete number of machine cycles.

In an alternative embodiment which does not have this infinite adjustment feature, several standard lengths of suture are accommodated by several standard positions which are fixed in the machine by pins which secure the cutter mechanism to the machine frame by pin receiving holes in the machine at the standard positions. For example, the cutter mechanism might be moved to a position for cutting 18" sutures and be secured to the frame by the placement pins being inserted into the pin receiving holes in the machine for 18" sutures. The cutter mechanism might also be moved to positions for cutting 27", 30", or 36" sutures by moving the placement pins to the pin receiving holes in the machine provided for those length sutures. Each different position can have a separate proximity switch provided therefor, which indicates the cutting mechanism position to the controller, which then downloads the appropriate servo gripper bottom position. The appropriate tipping mechanism position is known for each different cutter mechanism position.

FIGS. 9(a) and 9(b) illustrate a heater 362 in the tipping assembly 330 and the vertical movement of the suture 304(a) down (front view, FIG. 9(b) and through (top view, FIG. 9(a)) a suture tipping aperture 364, FIG. 9(a), positioned on the right side of the tipping assembly. FIG. 9(a) illustrates further details of the flow of heated air through the tipping assembly and its control to selectively heat and tip the suture. As described previously, the tipping assembly 330 is mounted near the top of the machine so that it takes a discrete number of machine cycles for the suture to reach the cut position. This gives the tipped area time to cool down before the cutting and insertion operations. The tipping assembly operates by flowing air supplied at a regulated pressure through an inlet air duct 366 at a regulated flow rate, in one embodiment 195 CFH (Cubic Feet per Hour), over a heater coil mounted within an outer heater casing 368. Air is supplied to a flowmeter at a regulated pressure required to maintain 195 CFH of air flowing over the heater coil. A thermocouple 370 is positioned in the air flow at the discharge end of the heater casing 368, to monitor and control the air temperature through a controller in a programmable logic controller (PLC). The tipping assembly 330 is operated at various temperatures between 200° F. and 550° F. depending upon the particular suture material to be run. The particular temperature is a down loaded parameter from an operating program at each suture batch changeover. The tipping assembly guides the suture and provides a 2.000" long heating aperture 364 for the tipping length.

The constant flow of heated air at the outlet of 368 flows either 1) through the heating aperture 364 in which the suture 304 is intermittently stopped and positioned during a tipping operation, or 2) alternatively the heated air is dumped into the surrounding atmosphere through a diverter channel 372, illustrated in FIG. 9(b). The flow of hot air is controlled by an air cylinder 374, under control of a solenoid 376, which controls the flow of actuating air through air tubes 378, 380. The air cylinder 374 controls the position of a retractable slide element having a flow aperture therein which is selectively positioned in front of either 1) a channel into the heating aperture 364 or 2) the diverter channel 372, depending upon the position of the slider element which is controlled by an air cylinder.

As an example, the following control parameters have been established for heat tipping of Braided VICRYL sutures sizes 1, 0, 2/0, 3/0 and 4/0. The suture tension refers to the tension force in grams which the tension roller 314 and torque motor 316 apply to the suture as it is being drawn through the machine by the grippers.

| Suture Size | Tipping Temp. +/− 25 deg. | Tipping Time +/− 25 Ms | Suture Tension +/− 25 Grams |
|---|---|---|---|
| 4/0 | 375 F. | 380 | 275 |
| 3/0 | 395 F. | 380 | 275 |
| 2/0 | 410 F. | 380 | 275 |
| 0 | 425 F. | 380 | 275 |
| 1 | 435 F. | 380 | 275 |

As a further example, the following control parameters have been established for suture tension and heat tipping of silk sutures sizes 2/0, 3/0 and 4/0. In the following table the left column lists commercial needle types, the next column needle sizes, the next column suture sizes, the next column suture tension in grams applied by the tension roller 314, the next column tipping dwell time, the next column tipping heated air flow in standard cubic feet per minute, and the right column suture tipping temperature.

| SILK SUTURE AND TIPPING PARAMETERS | | | | | | |
|---|---|---|---|---|---|---|
| Needle type | Wire Size (0.000") | Suture Size | Suture Tension (grams) | Tipping Dwell (seconds) | Tipping Air Flow (SCFM) | Temperature (°F.) |
| Tolerance | N/A | N/A | (±10 grams) | (±0.020) | (±5) | (±15) |
| CT-1 | 39 | 2–0 | 275 | 0.380 | 190 | 300 |
| CT-2 | 39 | 2–0 | 275 | 0.380 | 190 | 300 |
| SH | 26 | 2–0 | 275 | 0.380 | 190 | 300 |
| SH | 24 | 3–0 | 275 | 0.380 | 190 | 300 |
| SH | 22 | 4–0 | 275 | 0.380 | 190 | 300 |
| SH-1 | 22 | 3–0 | 275 | 0.380 | 190 | 300 |
| SH-1 | 18 | 4–0 | 275 | 0.380 | 190 | 300 |

The previous tables are for braided VICRYL suture and silk suture, and similar tables could be developed for other suture materials such as Ethibond® (braided polyester) and monofilament and braided nylon.

The suture drawing, tipping and cutting is more completely described in U.S. Ser. No. 08/804,478, U.S. Ser. No. 08/803,573, and U.S. Ser. No. 08/804,477, attorney dockets 8924Z, 8924Y, 8924X, all of which are entitled "Suture Cutting System," the disclosures of which are incorporated herein by reference thereto.

The Swage Dial Drive Assembly

Figure 7A:
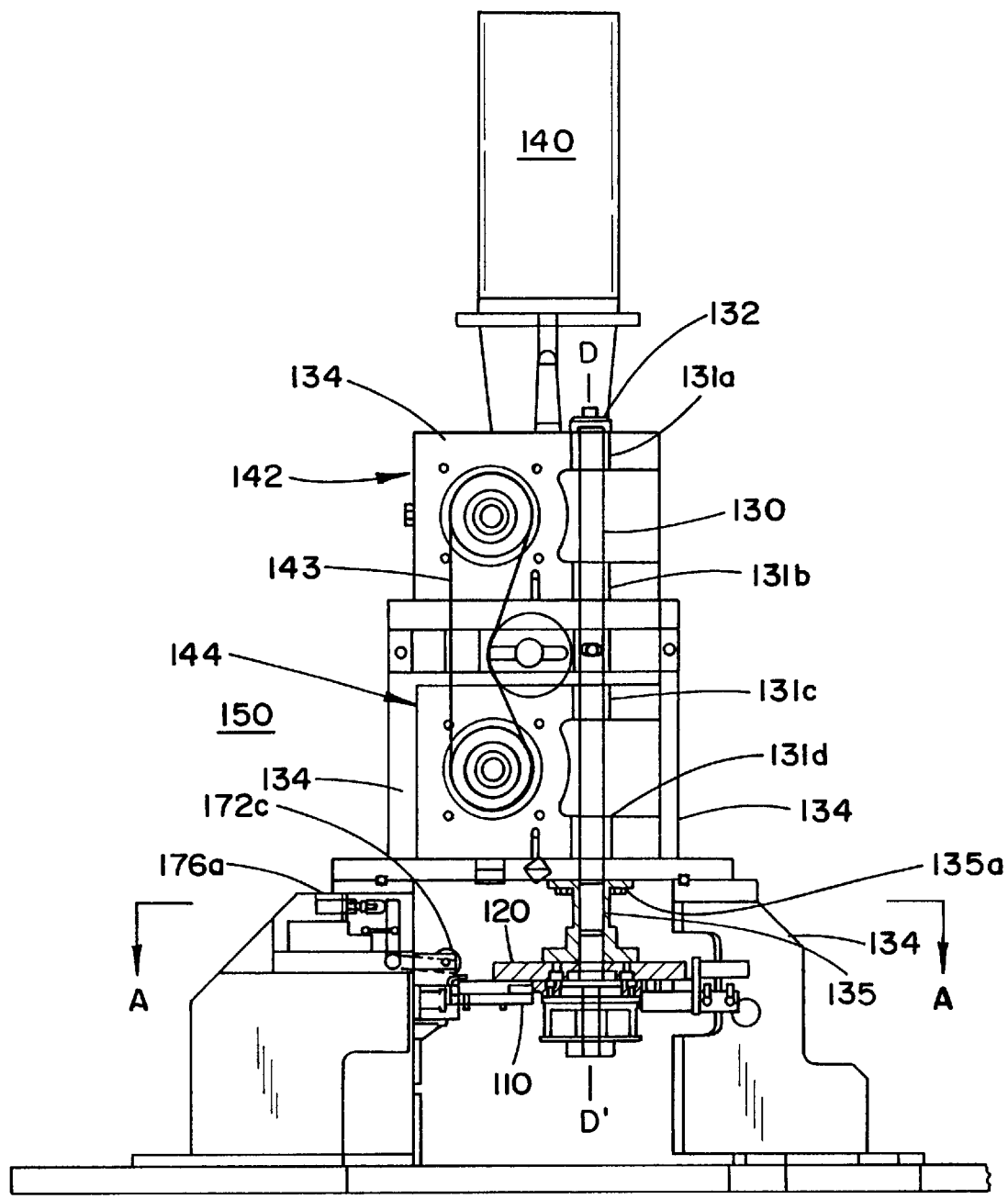
FIG. 7(a) is an elevation view of a portion the apparatus illustrating the inventive drive for the cam dial and swage dial of the present invention.
Figure 7B:
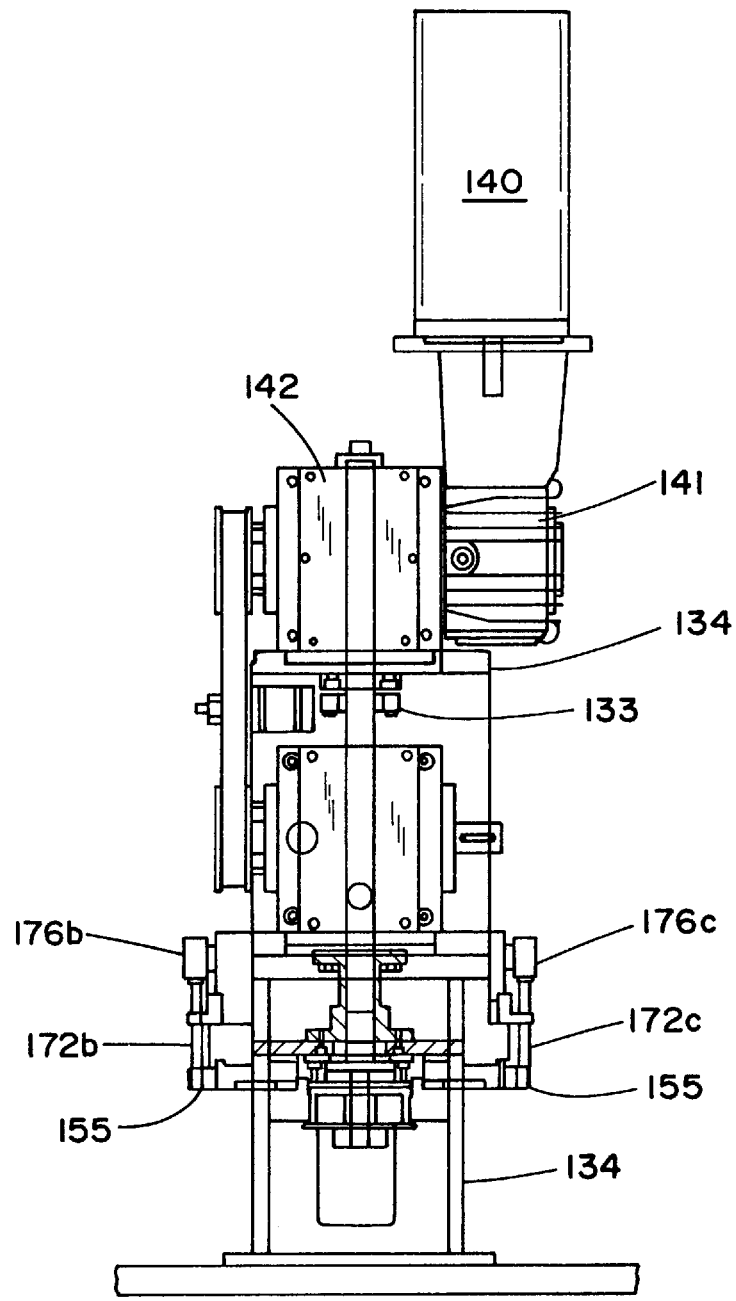
FIG. 7(b) is a side view of the drive for the swage dial illustrated in the elevation view of FIG. 7(a).
Figure 8:
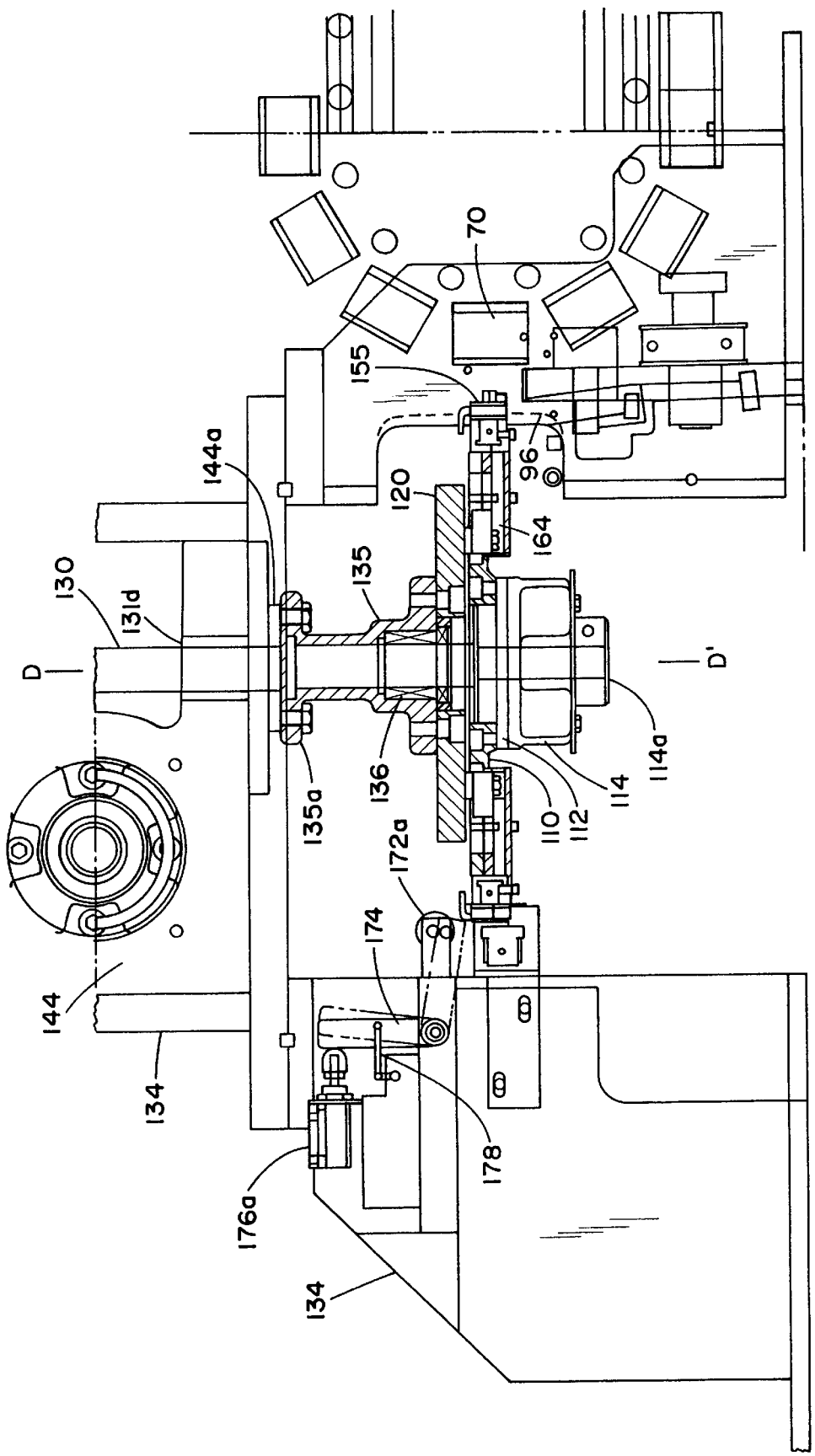
FIG. 8 is a detailed and partially cross section view of the drive for the swage dial taken along section lines "A"—"A" in FIG. 7(a) which illustrates a universal gripper ready to reciprocate outwardly to receive an oriented surgical needle from a precision conveyor.

The drive assembly for the swage dial 150 is illustrated in FIGS. 7a, 7b and 8. As illustrated in FIG. 7a, the swage dial assembly 150 includes a swage dial 110 and a cam dial assembly 120 both of which are independently driven by the drive means of the present invention. A drive motor 140 drives both of these dials through a first indexing drive transmission 142 and a second indexing drive transmission 144 through a 90° reduction transmission 141 and are coupled together with a timing belt 143. The indexing drive assemblies 142,144 are "CAMCO" Indexer Drivers Model 350RGD 4H24-360 with a 10 to 1 reduction in transmission 141 and an oscillation motion for the cam dial assembly 120.

As will be hereinafter explained with respect to FIGS. 10–11, the first indexing CAMCO drive includes 180° of drive and 180° of dwell for every revolution of the transmission drive 141 which results in a 90° drive dwell cycle for the first indexing drive 142. The first indexing drive 142 drives shaft 130 about a single drive axis D–D' illustrated in FIGS. 7–8. It is journalled for rotation in bearings 131a,b,c, and d and is secured in place by drive cap 132 and a compression drive collar 133 which is connected to the output of the first indexing drive 142. A modular frame assembly 134 supports each of the drive elements about the central drive axis D–D'.

The second indexing drive 144 also includes 180° of drive, a second 60° of drive, a 30° dwell, a 60° drive and a 30° dwell for each revolution of the input drive from belt means 143, and the indexing drive 144 is phased with the drive and dwell cycles of the first drive 142. As will be hereinafter described with respect to FIGS. 10 and 11, during each dwell period of the swage dial 110, the cam dial assembly 120 is held in a dwell position and then rotated to enable radial reciprocation of the universal grippers with respect to the swage dial 110.

The cam dial assembly 120 is mounted on an annular drive collar 135 which connects the output of the second indexing drive 144 to the cam dial plate 120 as more fully illustrated in FIG. 8. The annular drive 135 is journalled for rotation on drive shaft 130 by means of needle bearings 136 to provide a single drive access D–D' for rotation of the swage dial assembly 150. The annular drive collar provides suspension support and rotational drive for the cam dial assembly 120. The use of this annular collar also separates the cam dial and swage dial from the drive apparatus and enables operator workspace for alignment of the apparatus and for part changes when necessary. The annular drive collar 135 is bolted to the output drive flange of the indexing drive 144 as shone at 135(a).

The swage dial 110 is mounted for rotation on a ball detent clutch 114 which is fixably attached to shaft 130 and enables breakaway rotation between clutch drive plates 112 and 114 in the event of a catastrophic jam. The clutch 114 and shaft 130 also provide suspension support and rotational drive for the swage dial 110.

The annular cam drive 135 is bolted to the output of the second indexing drive 144 as illustrated at 135a and thus provides for both suspension support and rotation of the cam dial assembly 120. Likewise, the breakaway clutch 114 provides physical support and rotational drive for the swage dial 110 by virtue of its fixed mounting on shaft 130 at 114a.

The Swage Dial

Figure 11A:
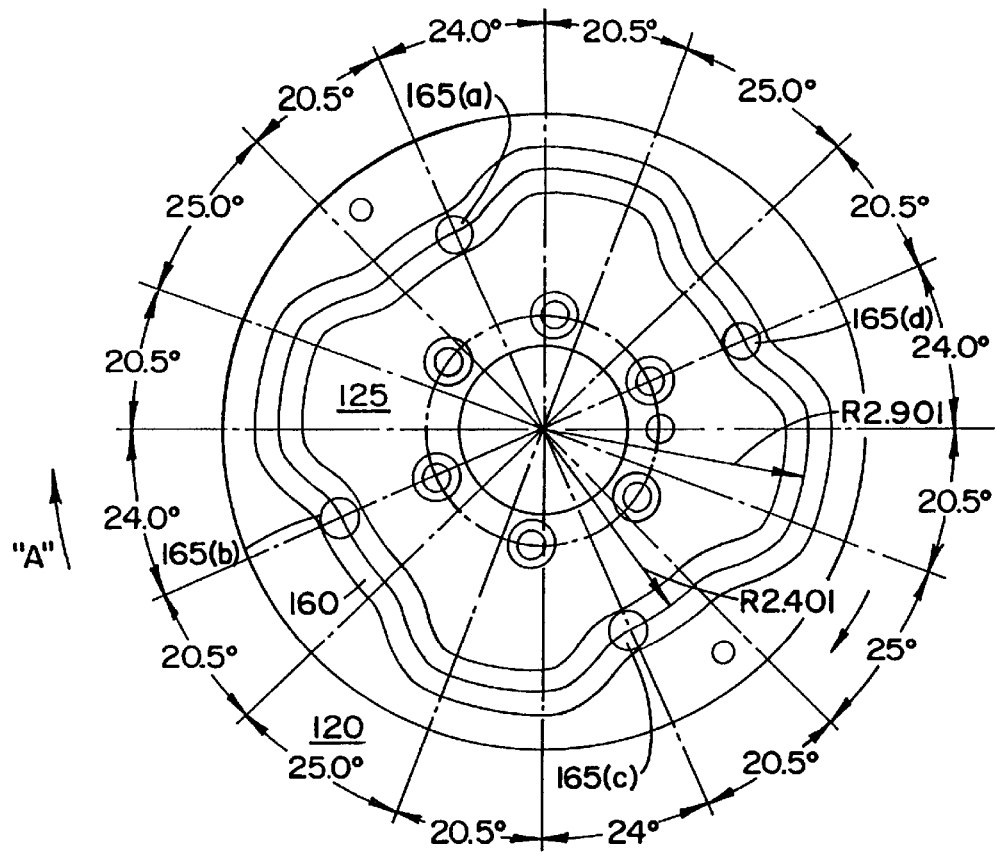

The process for extending each universal gripper 155 for needle processing at each of the stations 100, 200, 400, and 500 will now be explained. As shown in FIGS. 10(a), 10(b) and 10(c), each universal gripper 155 is connected to a reciprocating carriage 151 and a cam slide 164. Cam followers 165(a),(b),(c) and (d) are mounted to a cam slide 164 at one end thereof with the universal gripper at the other end. Cam slide 164 is slidable within stationary guides 166,167 and is adapted for reciprocal movement when the cam follower 165 is actuated. In the preferred embodiment shown in FIG. 11(a), cam followers 165(a)–(d) are rollers that fit within the cam track of a rotatable cam dial assembly 120. Cam dial assembly 120 is shown in FIG. 11(a) as comprising a cam dial plate 125 having a continuous cam tracks 160 which receives cam followers 165(a)–(d) attached to universal grippers 155a,b,c, and 155d, respectively. Each cam follower 165 is positioned within the cam track at each station for movement therein.

Figure 11B:
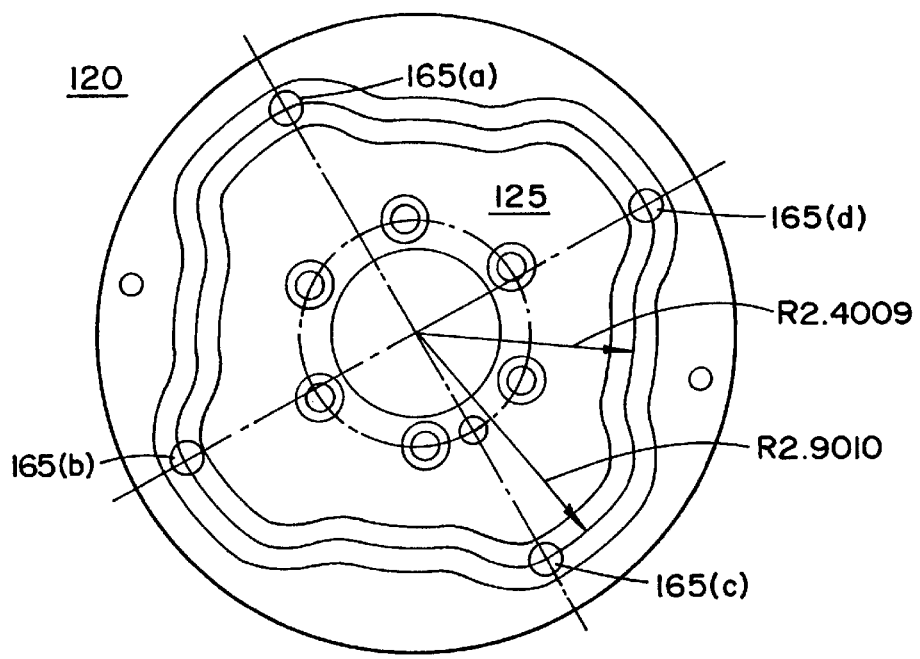

As illustrated in FIG. 11(a), cam dial 125 is positioned above swage dial 110 and mounted coaxial therewith. The cam dial 125 is rotatable about a central axis and controlled by a separate rotary indexing transmission as described previously so that it may rotate separately from the swage dial plate 110. The cam dial is driven in multiple drive and dwell cycles as previously explained, and the degrees of each phase are diagrammatically illustrated in FIG. 11(a). FIG. 11(a) also shows cam followers 165a–d in a first retracted position within the cam track 160. When the dials are in this position, each of the reciprocating carriages and consequently universal grippers 155 are in their retracted position as shown in FIG. 10(a) and 10(b) discussed above. To extend the universal grippers 155 in place at their respective stations, the cam dial plate 125 is rotated in the clockwise direction with respect to the swage dial plate 110, as indicated by the arrow A in FIG. 11(a), for approximately 25–45 degrees, forcing cam followers 165a–d in its cam track 160 to move toward the periphery of the dial as shown in FIG. 11(b). Consequently, each of the cam slides 164, reciprocating carriages 151a, and the universal grippers 155 move to the extended position as shown in FIG. 10(c). To move back to its retracted position, the cam dial plate 125 is rotated in the counter clockwise direction with respect to the swage dial plate 110 for approximately 20 to 30 degrees, forcing cam followers 165a–d in the cam track 160 to move to their retracted position (FIG. 11(a)). Consequently, the cam slide 164, reciprocating carriage 151a, and the universal gripper 155 move back to the retracted position as shown in FIG. 10(b) and discussed above.

It should be understood that when cam dial plate 125 rotates with respect to swage dial 110, each universal gripper 155 is either extended or retracted by the cam track. Thus, the system is designed so that all processes performed at each station occur simultaneously and for approximately the same duration of time when the universal grippers are in their extended position, for e.g., for needle pick-up, for needle swaging, or, for needle pull-testing.

When the universal gripper 155 is retracted, the needle engaged thereby may then be indexed to a different station for further processing. To index the needle to another station, both swage dial plate 110 and cam dial plate 125 are rotated together for approximately 90 degrees to position the universal gripper at the next station. For example, when the cam dial plate 125 and the swage dial plate 110 are simultaneously rotated 90 degrees counterclockwise in FIG. 10, the gripper 155 that had received the needle at station is now indexed to station 200 for swaging a suture thereto. Similarly, after swaging, the cam dial plate 125 and the swage dial plate 110 are simultaneously rotated counterclockwise so that the armed needle at station 200 is indexed to the pull-testing station 400 for pull-testing thereof. The operations performed concurrently at each station about the swage dial increases throughput to provide an output of pull-tested armed surgical needles at a rate of approximately 40 to 60 per minute in the preferred embodiment.

Universal Gripper

As illustrated in FIG. 1, the rotatable swage dial assembly 150 cooperates with four stations where simultaneous needle operations are performed. In the detailed illustration of FIG. 10(a), the swage dial assembly 150 includes a swage plate 110 having four universal gripper stations 145a, 145b, 145c, 145d spaced equally thereon.

The swage plate 110 is rotatably mounted at a central hub 112 on a ball detent safety clutch 114 (illustrated in FIG. 8) and operable to rotate under the control of a control system computer 46. In the preferred embodiment, a separate reciprocating carriage 151 is provided at each universal gripper station of the swage dial assembly 150. For instance, as shown in FIG. 10(a), universal gripper station 145a includes reciprocating carriage 151a, while station 145b includes reciprocating carriage 151b, station 145c includes reciprocating carriage 151c, and station 145d includes reciprocating carriage 151d. Mounted to each reciprocating carriage 151a, b,c,d for retractable movement therewith, is one universal gripper 155, two of which are shown connected to gripper mounts 150(a) and (d) in FIG. 10(a).

As previously mentioned, each reciprocating carriage 151a,b,c,d and universal gripper 155 connected thereto is movable from a retracted position to an extended position. When the gripper 155 is in the retracted position shown in FIG. 10(b), the needle 39 may be conveyed to a different station as the swage dial rotates; when the gripper 155 is in the extended position as shown in FIG. 10(c), the needle is in one of the active stations, such as the automatic swaging station.

The universal gripper of the present invention receives the needle from the precision conveyor and moveable hard stop mechanism, and transports the needle through the swage operation in which a suture is automatically inserted into the barrel end of the needle, and the metal of the needle swaged about the suture. As can be appreciated, when the opening in the barrel is only 0.0106 and the suture diameter is 0.0088, a high degree of precision handling is required, particularly so when the insertion and swage operation need to be completed in approximately 0.5 seconds in order to maintain a 30 to 60 needle per minute cycle rate. The universal gripper also transports the needle through the pull test station in which the suture bond is tested and to the packaging area, where the armed suture (needle and suture assembly) is bundled with other armed sutures for future packaging.

In FIGS. 14(a)(b) and (c), both the slide portion 164 and the gripper portion of the universal gripper 155 are illustrated, with a pair of needle gripping jaws 146 and 148, each having a portion of a needle receiving indent 157 formed therein. Each of the jaws have a reciprocal slide portion 146(a), 148(a) formed as an integral part, which slides reciprocate in a channel 162 formed in housing member 174, The jaws 146 and 148 are biased to each other and to a closed position by a spring member 160. The jaws are opened by a pair of moveable pivot linkages 166, 168 which are mounted to and actuated by plunger 170, so that when plunger 170 is depressed, the linkages 166, 168 are moved outwardly, drawing the jaws 146 and 148 with them. The plunger 170 is actuated by a cam driven by an air motor at each automatic station to open and close the jaws about a needle 39.

In the apparatus, a plurality of universal grippers are employed, preferably 4, each of which grips a single needle at positioning, at swaging, at testing and at off-load, as previously described. As the universal gripper is moved into position, the jaws 146,147 are opened and the gripper is reciprocated towards the needle so that open jaws are presented on each side of the needle. The jaws of the precision conveyor boat 70 are then opened, and during transfer, the needle rests on the moveable hard stop 96. The jaws 146,148 of the universal gripper are then closed to grip the needle and the moveable hard stop 96 is reciprocated out of engagement with the needle, and away from the jaws of the precision conveyor to allow the precision conveyor to advance the next needle into the needle transfer position.

The step of loading of the individual precisely oriented surgical needle 39 from the precision conveyor boat 70 and the moveable hard stop 96 onto the universal gripper 155 at the precision loading station 100 involves a compound movement on the part of the universal gripper. Since the needle is gripped in detents formed in the jaws of the conveyor boat 70, and since one of the jaws of the precision conveyor boat 70 is fixed, it is necessary for the universal gripper to transcend a compound movement when removing the needle from the conveyor boat jaws. If a straight reciprocal movement is attempted, the needle is stripped from the jaws of the universal conveyor by the detent in the fixed jaw of the conveyor boat 70. This compound movement is found at both the precision position station 100 and the swage station 200, which also uses fixed and moveable jaws. The use of a fixed jaw substantially improves the accuracy of the alignment of the needle with the suture at the swage station.

Figure 15A:
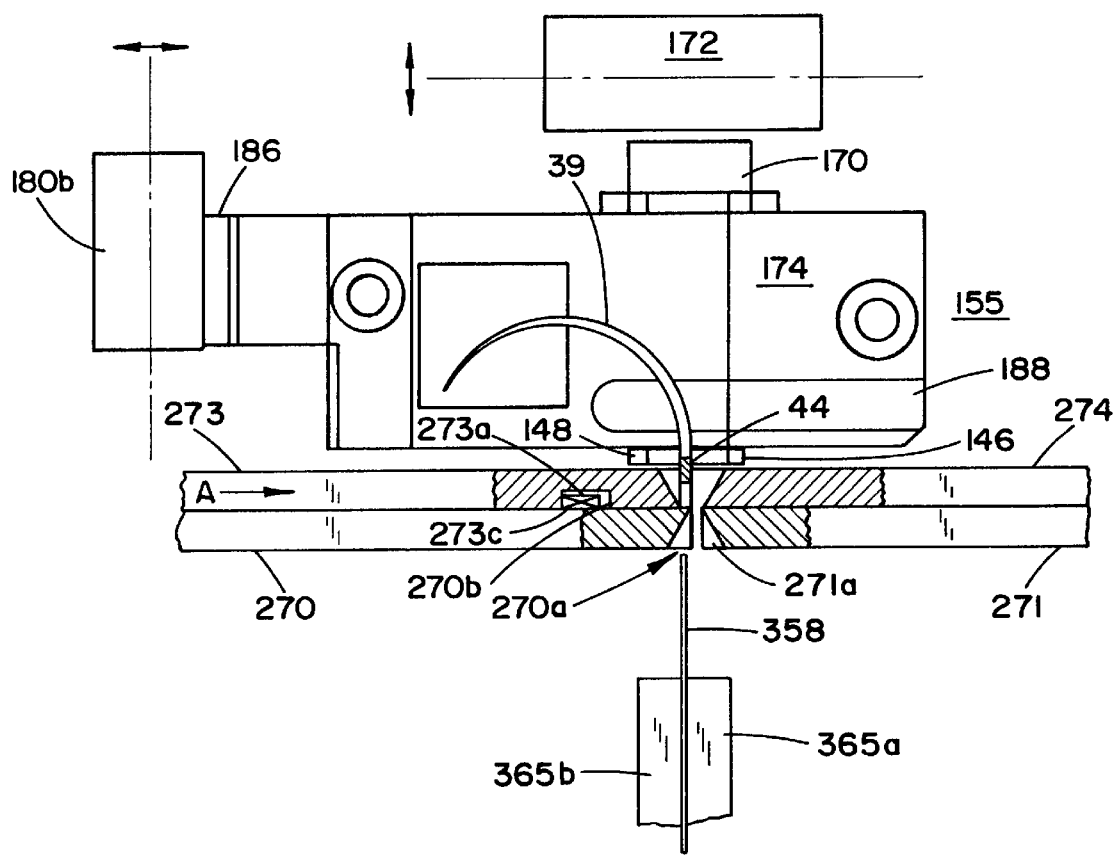
FIG. 15(a) is front face view of the universal gripper showing a surgical needle about to be placed in the swage dies of the present invention.
Figure 15B:
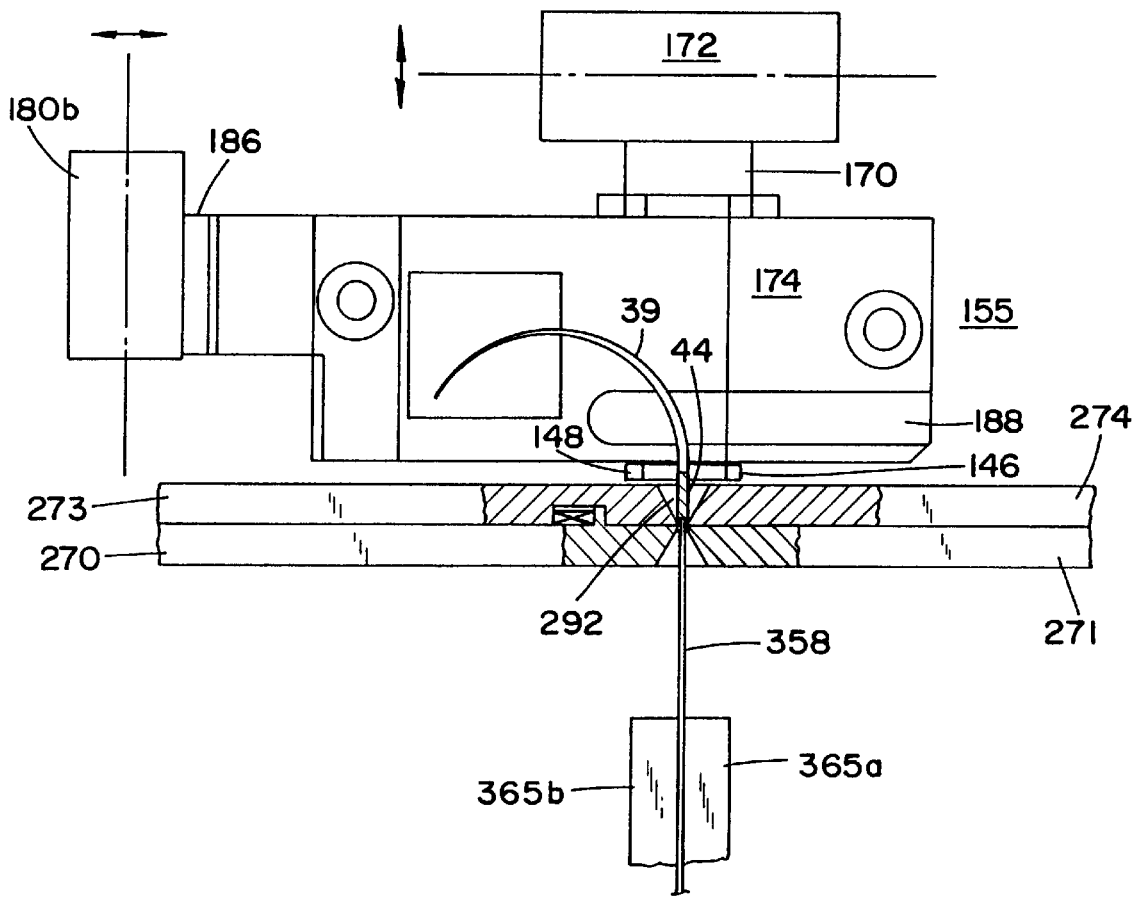
FIG. 15(b) is front face view of the universal gripper and a surgical needle with the universal gripper in a relaxed engagement, with the needle gripped by the swage dies of the present invention.

In the frontal view of the universal gripper as shown in FIGS. 15(a) and (b), jaws 146 and 148 of the universal gripper 155 extend perpendicularly from the gripper to engage the barrel end 44 of the arcuate needle 39.

FIGS. 15 (a),(b) also illustrates two roller cam surfaces 172, 180 which act on the universal gripper. A cam surface 172 is found at each of the four stations,(Precise positioning, swage, test and off-load) and is used to open jaws 146 and 148 of the universal gripper at each station. FIGS. 7 and 8 also illustrate three pneumatic drives 176(a),(b) and(c) which actuate rollers 172(a),(b) and (c) to open and close the jaws of the universal gripper 155 as will be hereinafter explained in greater detail.

FIG. 8 illustrates a typical positioning for cam 172 above the needle pull test station, wherein cam roller 172(a) is mounted on a bell crank 174, which is actuated by an air cylinder 176(a). The cam 172(a) is normally biased to a non-engaged position by spring 178.

Each of the universal grippers 155 is mounted for linear movement with respect to the cam slide 164 by means of an off-set slide assembly, the details of which will be explained as with respect to FIGS. 14(a), (b) and (c). As indicated therein, the housing 174 of the universal gripper is mounted on a mounting block 175 and slide 177, and slide 177 is spring biased to a home position during reciprocation within slide carriage 151 by spring member 179. This second reciprocal movement is transverse to the reciprocal movement imparted by cam slide 164.

Referring to FIG. 15(a),(b), roller cam 180 is used to provide the compound off-set movement of the universal gripper as it is reciprocated outwardly by the swage dial cam plate 125. FIG. 10(a) illustrates a typical positioning for the offset drive used to drive cam roller 180 at the precise positioning station 100. Roller cam 180 is mounted on a linear slide 182, which is driven by an air motor 184, mounted on the swage dial frame. FIG. 10(a) also illustrates the relative motions of the universal gripper 155, with arrow A indicating the off-set movement, arrow B indicating the reciprocal movement which results in the radial reciprocation of the universal gripper 155 to 155a in FIG. 10(a), and arrow C indicating the rotary motion of the swage dial 110.

To accomplish the transfer of the needle to a universal gripper 155, the universal gripper 155 is extended and translated horizontally so that the face of the universal gripper is adjacent to the needle precision conveyor boat 70 as shown in FIGS. 8 and 10(a). In this position, the jaws 146 and 148 penetrate the plane of the needle 39 on either side thereof. A load solenoid or similar device depresses a pusher arm of the precision conveyor boat 70 to release the needle from the engagement jaws 77,79 of the precision conveyor boat 70 so that it rests on the movable hard stop assembly between jaws 146 and 148 of the universal gripper 155. Simultaneously therewith, as controlled by the control system computer, jaws 146 and 148 are actuated from the non-engaging position to an engaging position to thereby engage the needle 39 in an oriented position as shown in FIG. 15(*a*). The universal gripper 155 is then off-set horizontally and retracted radially and the swage dial assembly 150 is rotated to the swaging station 200 to accomplish automatic swaging of the suture to the needle 39.

Needle Swaging Station

The swaging operation taking place at the swaging station will now be described with reference to FIG. 12, FIGS. 15(*a*)–(*b*) and FIGS. 19(*a*)–(*c*). FIGS. 15(*a*)–15(*b*) illustrate the universal needle gripper 155 and swaging and suture alignment dies shown in two stages of the suture insertion and needle swaging sequence. This sequence, and the interaction of the dies in relation to each other, the needle, and the insertion of the suture, accomplish the insert and swage function with minimal parts changes for each group of needle diameters and simple motions.

Figure 12:
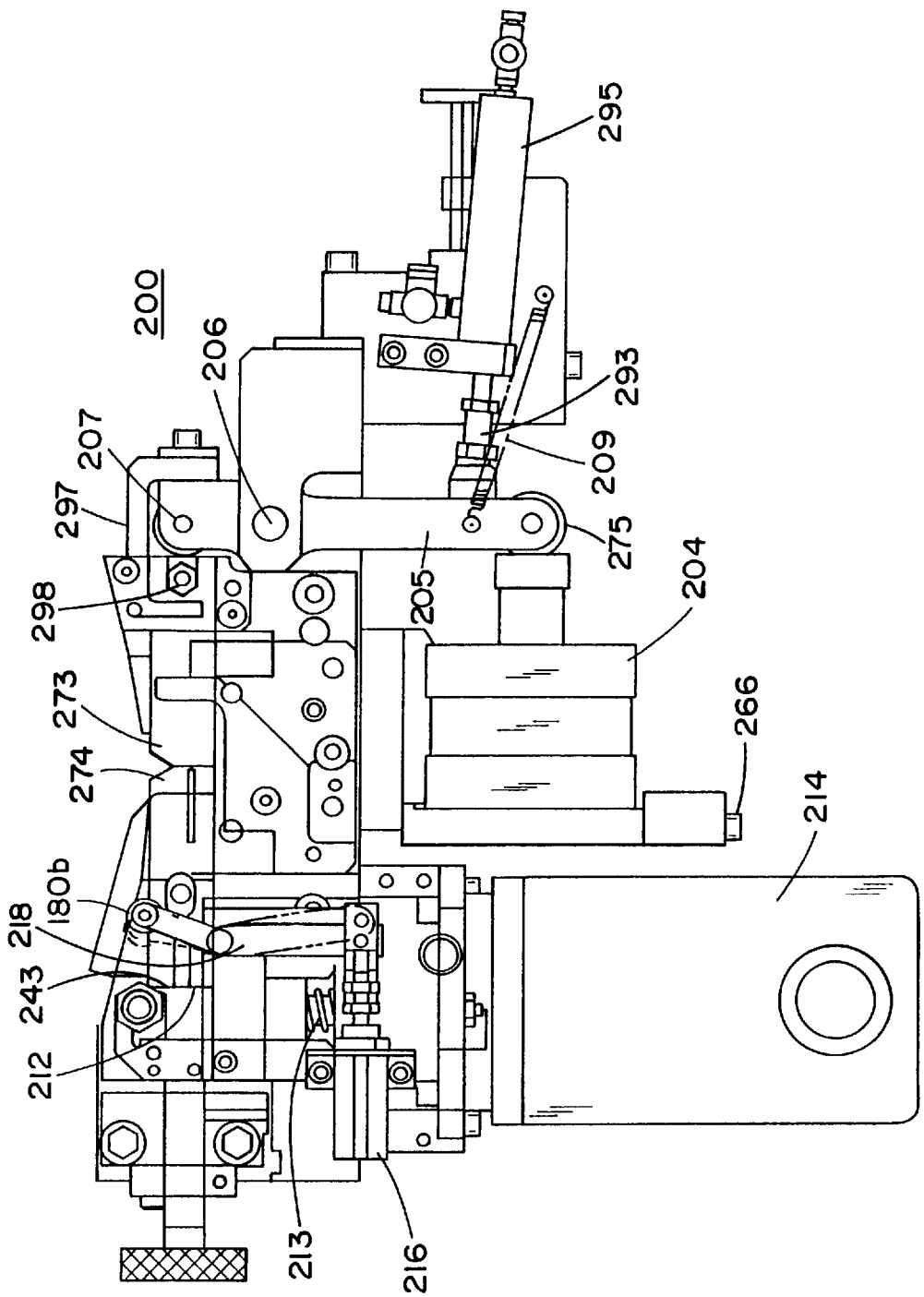
FIG. 12 is a top plan view of the swage assembly and off-set assembly of the present invention used for swaging the needles for suture attachment.

After conveying the needle to swaging assembly 200 shown in FIGS. 12 and 15(*a*), the universal gripper 155 is radially extended from the swage dial, and off-set to the side in the manner described above to position the suture receiving end 44 of needle 39 between the funnel shaped die opening formed at the ends of two swage dies 273,274 as shown in FIG. 15(*a*). As will be explained, swage die 274 is relatively fixed in position and swage die 273 is movable laterally toward the fixed swage die 274, as indicated by the arrow "A", to accomplish swaging of the suture receiving end of a needle placed therebetween. A funnel shaped die opening having an exit diameter slightly larger than the diameter of the suture receiving end 44 of the needle is formed when the two swage dies 273,274 are positioned adjacent each other as shown in FIGS. 15(*b*).

In the preferred embodiment shown in FIGS. 19(*a*) and 19(*b*), the ends of each of the swage dies 273,274 are provided with rectangular die cavities 283,284 respectively, to permanently swage the suture to needle 39. Note that as illustrated in FIGS. 19(*a*),(*b*), The swage dies are for a small 18 mil needle, and FIG. 19(*a*) has been magnified 2× and FIG. 19(*b*) magnified 100× for purposes of illustration. Different sets of swage dies may be provided, depending upon the size (diameters) of the needles and sutures to be swaged, and in the practice of the present invention, dies for needles ranging from 18 mil (0.018) to 50 mil (0.050). The die cavities illustrated in FIGS. 19(*a*),(*b*) are rectangular in shape with a 90 degree angle, and used to impart a permanent swage bond between needle and suture. Similar dies may be used with round die faces to impart a controlled release swage bond between the needle and suture.

To precisely position the suture receiving end 44 of needle 39 between the swage die opening formed at the ends of two swaging dies 273,274, the movable swage die 273 is temporarily moved apart. In the illustration of the swaging assembly 200 shown in FIG. 12 and 15(*a*), swage die 273 is moved apart from the fixed swage die 274 by actuating air cylinder 295 to provide a force upon cylinder rod 293 to enable swage die operating lever 205 to pivot about pin 206 and pull a retraction arm 297 which engages stud 298 affixed to moveable swage die 273 a predetermined distance away from the fixed swage die 274. In the preferred embodiment, lever 205 is biased by spring 209 so that the movable swage die 273 will return toward the fixed swage die by the spring restoring force when the pressure provided by the air cylinder 295 is terminated.

FIG. 15(*a*) shows die 274 in its fixed position, and moveable die 273 in its spaced apart position prior to receiving the surgical needle 39 presented by universal gripper 155. Suture alignment die 270 containing suture guide funnel half 270(*a*) is positioned under swage die 273, and free to slide laterally within limits. Suture alignment die 270 has a tang 270(*b*) that protrudes into cavity 273*a* formed within swage die 273. Compression spring 273*c* bears against the back wall of cavity 273*a* and tang 270(*b*) such that funnel die 270(*a*) slides forward until it is constrained by the inner wall of cavity 273(*a*). In this position, it is forward of the center axis defined by the suture receiving end of the needle, and serves; as a shelf that helps assure suture receiving end 44 of needle 39 is in position for swaging. In this stage of the cycle, the parts are not positioned for suture insertion, and suture clamps 365(*a*), (*b*) gripping suture 304 and stiffened end 358, are in dwell. Suture alignment die 271, containing funnel half 271(*a*), is fastened to swage die 274 by suitable fastening means.

While the swage dies are apart, the universal gripper 155 is extended to position the suture receiving end 44 of needle 39 within the swage opening as shown in FIG. 15(*a*). Referring to FIG. 12, the universal gripper is off-set during entry and egress by cam roller 180(*b*), which is driven by air cylinder 216 through bell crank 218. This off-set is necessary to allow the needle to box step into the swage die opening 284 in the fixed swage die as it is placed in position by the universal gripper 155. After positioning the suture receiving opening 44 of needle 39 at the swage die opening 284, the moveable swage die 273 is moved toward needle 39 with the resilient spring force present in spring 209 that is sufficient to enable the dies 273,274 to grip and locate the suture receiving end 44 precisely against fixed swage die 274 without deforming the cavity of the suture receiving opening 44 formed therein. Concurrently, the jaws 146,148 of universal gripper 155 are opened by downward external force on plunger 170, by cam roller 172 as described above, thereby releasing the needle so that its position is determined by the grip of sweaging dies 273 and 274. The motion of dies 273 and 270 causes the face of suture alignment die 270 to come in contact with the corresponding face of suture alignment die 271. The resilient force causing this motion is forceful enough to compress spring 273*c*, and move funnel die 270(*a*) to the left, such that tang 270(*b*) is no longer in contact with cavity wall 273(*a*). Dimensioning of dies 270 and 271 is such that this motion results in the formation of two funnel halves 270(*a*) and 271(*a*) defining a smooth conical shape that is coaxial with the suture receiving end 44 of needle 39.

FIG. 15(*b*) illustrates suture grippers 365(*a*), (*b*) moved vertically to the insertion position, which causes stiffened suture end 358 to enter the funnel defined at 270(*a*), 271(*a*), and be guided into the suture receiving cavity 44 of needle 39 axially aligned therewith. Note that the exit diameter of the conically shaped funnel guide formed of funnel halves 270(*a*) and 271(*a*) is preferably equal to or greater than the diameter of the suture tipped end 358 and smaller than the diameter of the suture receiving end 44 of the needle 39, so that the tipped end 358 of the suture strand may be easily inserted therein. An enlarged detail of the suture alignment dies 270,271 and the placement of the funnel portions 270(*a*)

and 271(*a*) is illustrated in FIG. 19(*c*). Once the strand is inserted into the suture receiving end 44 of the needle (step 27) as discussed above, the automatic swaging of the suture receiving cavity occurs.

In the preferred embodiment of the swaging assembly 200 shown in FIG. 12, a pneumatic air cylinder 204 provides air pressure to actuate cam 275 that bears on lever 205 to pivot about pivot point 206 and drive cam 207 against the end of the moveable swage die 273 to thrust movable swage die 273 toward the fixed swage die to accomplish the swaging of the suture receiving end of the needle placed therebetween. Air pressure is supplied to the swage cylinder 204 via ports 266 under the control of the control system computer 46.

After the swage die 273 has been driven to a fixed stop by the swage cylinder, the suture receiving end 44 of needle 39 has been deformed to the desired shape defined by the swage die contours, as illustrated in FIG. 19(*b*). As deformation takes place, the moveable swage die 273 comes to a stop as a swage stop post which is press fit into the moveable swage die 273 strikes a reference wall cross milled into the frame of the swage assembly. When the swage stroke is performed, the swage cylinder drives the die and post assembly to the left (in FIG. 12) until it is positively stopped by the lower portion of post striking the wall of the cross milled groove in the assembly frame (located under swage die 273 in FIG. 12). This stalls air cylinder 204, so that the stroke of the moveable right hand die assembly shown is always the same for repeated cycles of the machine. In an alternative embodiment, both swage dies 273,274 may be movable towards each other to accomplish swaging.

In the preferred embodiment, the degree of swage compression imparted on the needle, and resulting strength of grip by the needle on the suture, is adjusted by precise positioning of the fixed die 274.

As shown in FIG. 12, servomotor 214 rotates a swage adjust screw 213. by driving a belt and reduction pulley on the end of swage adjust screw 213. The pitch of the swage adjust screw 213 is selected to move a sliding wedge 212 a small distance. The swage die 274 has a complementary ramp angle 243 at the opposite end which bears on the wedge 212 to retract or advance the position of the swage die 274 a precise distance proportional to the movement of the sliding wedge. Thus, the rotation of the swage adjust screw 213 and motion of the sliding wedge 212, results in transverse movement of the swage die 274 to thereby finely adjust its fixed position. For example, when a larger suture is to be swaged to a needle, the position of the fixed die 274 may be moved further away from the suture drawing axis so as to provide the desired amount of deformation when the swaging pressure is applied to the needle by the movable swage die 273. In the preferred embodiment shown in FIG. 12, the control system computer 46 will send the appropriate signals to automatically direct the servomotor 214 to adjust the position of the swage adjust screw 213, and hence, the position of the fixed die 274, in accordance with the pull-out test values of the needle-suture bond as measured by automatic pull-test system as explained in further detail below.

Specifically, appropriate control signals may be generated to direct the servomotor 214 to adjust the rotational position of the swage adjust screw 213 in accordance with stored statistical results of the pull-testing occurring at the pull-test station. Automatic pull-testing of the armed needle is desirable to ensure that the upstream swaging dies are optimally positioned to avoid over-swaging the needle-suture bond and hence, preventing the likelihood of clip-off, and, to avoid under-swaging the needle-suture bond to prevent the chance of pull-out.

Referring to FIG. 15(*a*), after the needle has been swaged to the suture, the universal gripper 155 closes jaws 146,148 on needle barrel end 44 as the drive roller 172 is reciprocated out of engagement with plunger 170. Simultaneously therewith, the moveable swage plate 273 is retracted to enable movement of needle 39 by the universal gripper 155. Before the swage dial 110 is rotated, the offset drive cam roller 180(*b*) is again advanced to bear against cam plate 186 and provide egress of the needle 39 from the swage dye cavity in fixed swage plate 274. Once the universal gripper 155 and needle 39 have cleared the fixed swage plate, the cam dial assembly 120 is rotated advancing cam rollers 165 inwardly to retract the universal grippers 155 in a radial direction and enable rotation of the swage dial 110.

Automatic Pull Test Station

The automatic pull-test station 400 that provides automatic pull-testing of a surgical needle and suture assembly is shown generally in FIGS. 20 through 24. As illustrated in FIG. 20 the automatic pull-test assembly 400 generally comprises a load cell mounting assembly 430 for mounting a load cell 435 which responds to loading of a V-plate needle arm 436 which receives the armed needle 39 from the universal gripper 155. A needle release cam roller 172(*a*) is provided for relaxing the armed needle from the grip of the universal gripper 155. A pull-test fence assembly 440 is provided to prevent the armed needle 39 from tipping over or becoming misaligned when the armed needle is relaxed.

The suture gripping assembly 470 includes two pairs of retractable grippers 425*a,b* and 426*a,b* for gripping the suture during the pull-tests. Grippers 425*a,b* are operatively connected to the weighted slide block assembly 472 for performing non-destructive pull-tests as will be described with respect to FIGS. 21 and 23. Two separate pneumatic cylinders are used to drive grippers 426*a,b* for destructive pull-tests.

A detailed description of each of these assemblies and their interaction will be explained in detail hereinbelow.

As shown in FIG. 20, a surgical needle 39 with attached suture is retained by a universal gripper 155 and, in the manner described above, is indexed to the automatic pull test station 400 by the rotary swage dial 150 to the position illustrated in FIG. 20. To position the armed needle 39 in the load cell 435, the universal gripper is extended from the swage dial 150 from center line "A" to center line "B" so that the end portion 44 of needle 39 is positioned above a corresponding receiving V-plate arm 436(*a*) of the load cell assembly 430 as shown in FIG. 20.

Figure 22A:
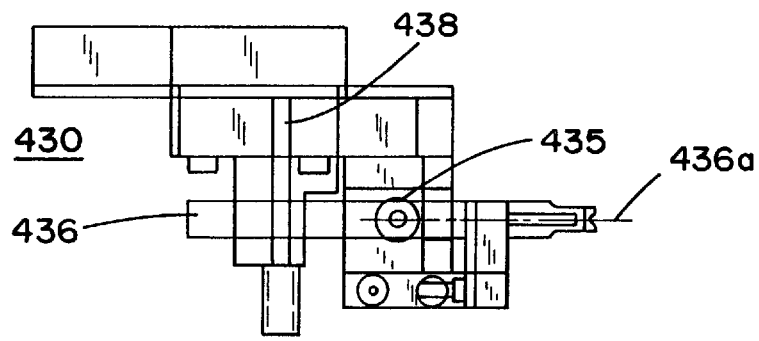
FIG. 22(a) is a plan view of the load cell assembly of the present invention, illustrating the v-plate needle arm.
Figure 22B:
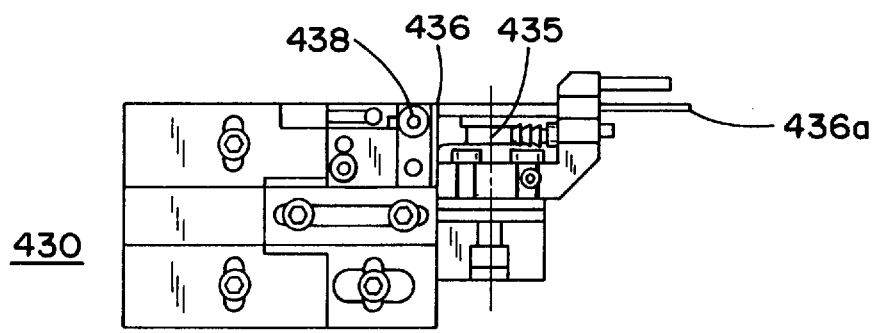
FIG. 22(b) is an elevation view of the load cell assembly of the present invention, illustrating the v-plate needle arm.
Figure 23:
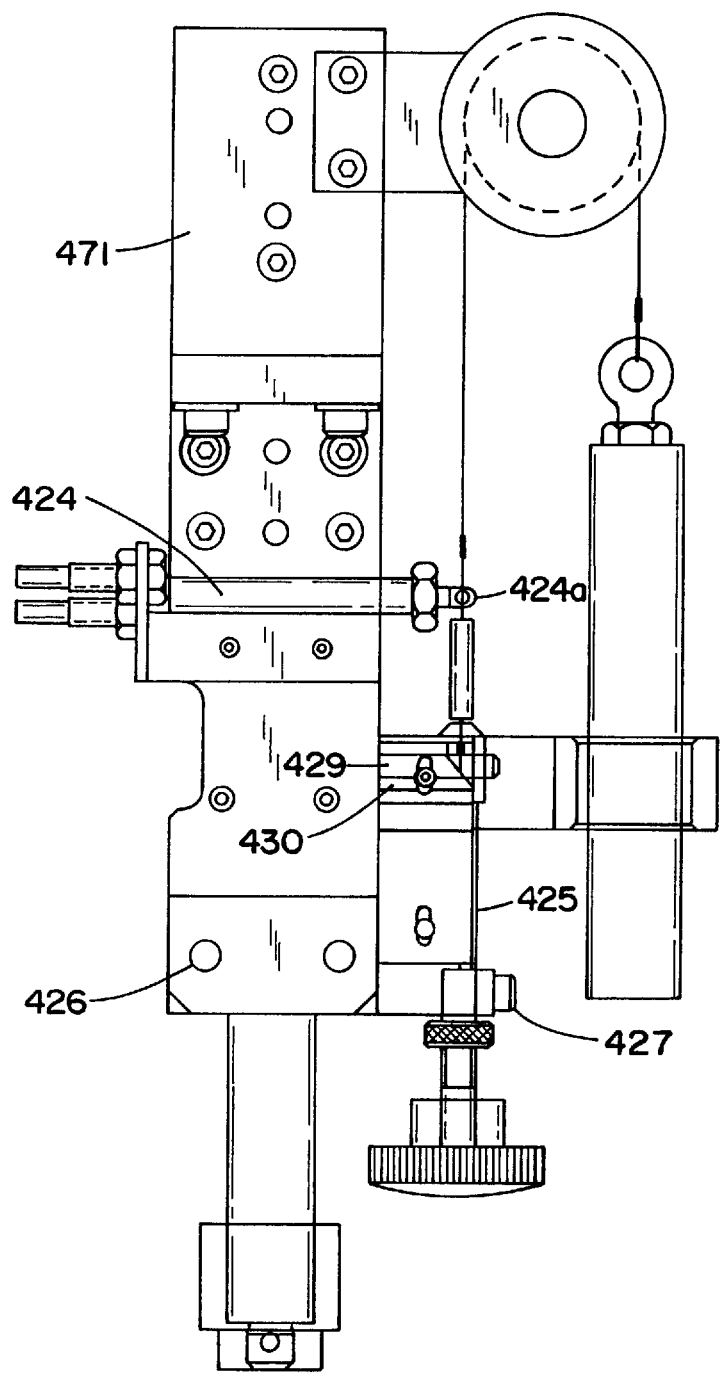
FIG. 23 is a rear elevation view of the pull test assembly illustrated in FIGS. 21(a) and 21(b) illustrating the spring tension assembly used for non-destructive pull tests.

FIG. 22(*a*) illustrates a top view of the load cell assembly 430 with load cell 435 mounted thereon. In the preferred embodiment, load cell 435 is loaded by a pivotally mounted V-plate needle arm 436 having a thin needle supporting blade 436(*a*) for supporting the suture receiving end portion 44 of various size surgical needles with the suture material 304(*b*) depending therefrom. Different V-plate arms may be provided for different needle suture combinations which accommodate larger and smaller sutures having diameters of approximately 0.009 to 0.017+/−0.001 inches. Depending upon the batch of surgical needles currently being pull tested, the appropriate needle V-plate supporting arm 436 will be positioned to receive the needle from the universal gripper.

Non-destructive pull testing of the armed surgical needle 39 is accomplished as follows:

After positioning the universal gripper 155 in the extended position as heretofore described, grippers 425a,b of suture gripping assembly 470 are closed from an open position to grip the suture strand slightly below the needle V-plate supporting arm 436 Of load cell assembly 430 as shown in FIG. 20. A single pneumatic actuator 472 (illustrated in FIG. 21(a)) is provided for opening and closing gripper arms 425a,b and the cylinder is controlled by a control system program resident in control system computer 46 as explained in further detail in copending patent application U.S. Ser. No. 08/804,476 (attorney docket No. 10193) assigned to the same assignee of the present invention, the disclosure of which is incorporated herein by reference thereto.

Figure 21A:
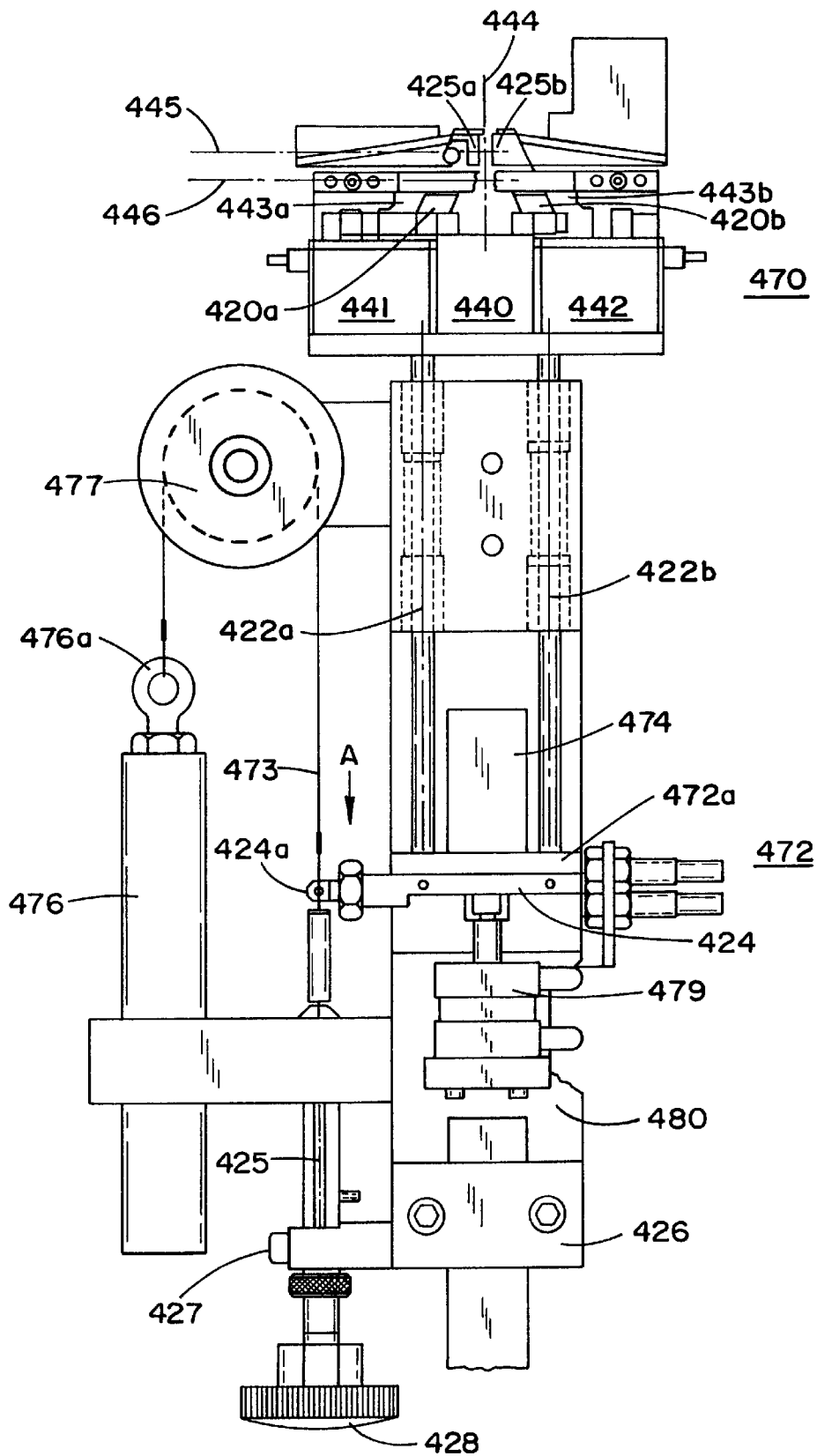
FIG. 21(a) is a front elevation view of the pull-test assembly illustrating the gripper assembly and the slide block assembly.
Figure 21B:
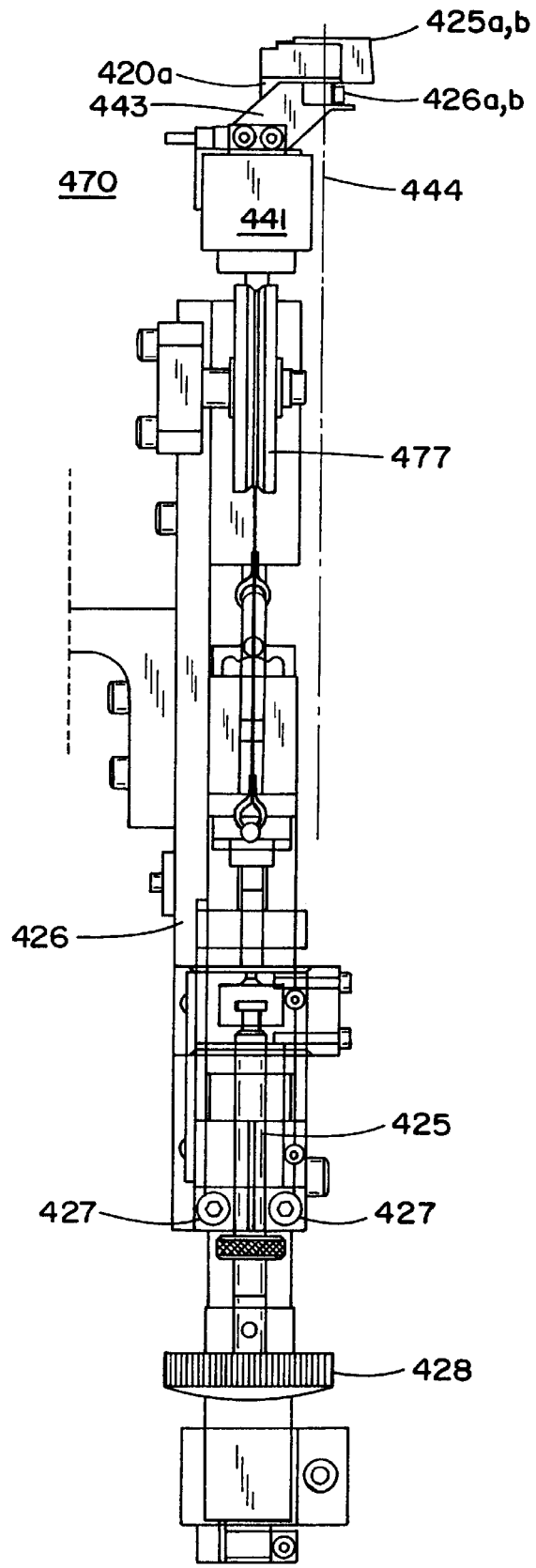
FIG. 21(b) is a side elevation view of the pull test assembly of FIG. 21(a) illustrating the gripper assembly and the slide block assembly.

FIGS. 21(a) and 21(b) illustrate the slide block assembly 472 that is composed of slide rods 422a,b and a lower slide block 472a which reciprocates vertically on the slide rods 422a,b. Slide block 472a includes a load balancing plate 424 upon which air cylinders 474, 479, apply respective upward and downward forces depending upon the type of pull-test that is to be performed. As shown in FIG. 20, air cylinder 479 is shown in an extended position providing an upward force that supports the load balance plate 424 and consequently maintains slide block 472a of slide assembly 472 at a fixed vertical position.

Slide block 472a is counterweighted to a net zero weight by appropriately sized counterweight 476 that is attached to the load balance plate at 424(a) and acts through cable 473, around pulley 477, and to attachment point 476a. This counterweight 476 acts to balance the net load on slide block 472a to a neutral position. An adjustable net downward force of 2 to 30 oz. is provided by an adjustable spring tension device 425, which is more clearly illustrated in FIG. 23. One end of spring tension device 425 is mounted to fixed position on the frame 426 by a mounting bolts 427. The other end of spring tension device 425 is attached to the load balancing plate 424 at 424a and exerts an adjustable downward loading between the load balance plate 424 and the fixed frame member 426. This adjustable download tension is normally offset by air motor 479 which drives the lower slide block 424 upward to a home position.

The amount of spring tension applied during a non-destructive pull-test can be varied from 2 to 30 oz. by rotation of knob 428 and the effective pull test loading is indicated by pointer 429 on scale 430.

To accomplish the non-destructive pull test, air cylinder 479, mounted on sub frame 480 and controlled by system computer 46, is relaxed from its extended position (FIG. 21(a)) supporting the load balance plate 424. This removes the upward force on load balancing plate 424 as shown in FIG. 21(a), to thereby impose the selected spring tension net weight of 2 to 30 ounces downwardly on slide block 472a and through slide rods 422a,b to the gripper assembly 470 and the gripper jaws 425a,b to pull downwardly on the suture attached to swage needle 39, in the direction of arrow "A". The accuracy of this system is enhanced because slide block 472 is suspended on slide rods 422a,b which are mounted in low friction ball bushings, pressed into frame member 471, thereby imposing minimal mechanical drag on the system.

Note in FIG. 20, that the fixed slide block frame 426 is positioned parallel to the axis 444 of the suture depending from the needle 39, and is located a distance away from the axis corresponding to the length of the offset arms 420a,b of gripper jaws 425a,b.

Simultaneous with or momentarily before the slide assembly 472 is released, the needle release cam roller 172(a) is actuated to enable universal gripper 155 to disengage its grip on the armed needle 39. Releasing the armed needle from the grip of the gripper 155 is necessary to ensure that it is firmly positioned on the V-plate needle supporting blade at 436(a). Moreover, to provide an accurate pull-test, the needle must be released so that there is no existing upward force that would cause false results.

As shown in FIGS. 8 and 20, the needle release cam roller assembly comprises needle release solenoid 176(a) that is actuated to rotate pivotal lever arm 174. Pivotal lever arm 174 pivots about pin 174(a) to depress plunger 170 of the universal gripper 155 as previously described with respect to FIGS. 15(a),(b). As was described with respect to FIG. 14, depressing plunger 170 opens jaws 146, 148 to release the needle 39 engaged therein.

Referring to FIG. 20, to prevent the needle 39 from becoming misaligned or from tipping over after the universal gripper 155 releases its grip on the needle, a needle fence assembly 440 is provided. As shown in FIG. 20, the needle fence assembly 440 includes vertical fence plate 442 which can be adjusted to lie a needle's diameter away from the face of gripper 155, and thereby retains the needle in an upright position for the test. Adjusting the lateral positioning of the vertical fence plate 442 is accomplished by rotating lead screws 443 (shown in FIG. 20) to advance or retract the fence for an appropriate distance. In the preferred embodiment, the configuration of the face of the vertical needle fence plate 442 (not shown) may be changed to accommodate the configurations of different size needles.

The controlled release of the minimum pull-test is of short duration, preferably ranging in milliseconds. If the test is successful, i.e., the suture meets the minimum pull-test requirements, the needle is re-gripped by the universal gripper 155 by deactuating the needle release solenoid 176(a) which retracts the cam roller 172(a) and releases the downward force on plunger 170. The suture gripper jaws 425a,b are then retracted to their open position to release their grip on the suture as controlled by the control system. Subsequently, the universal gripper 155 is retracted and the rotary swage dial 150 and rotated to convey the armed needle downstream for bundling.

If the suture fails the minimum pull-test, i.e., if the suture is dislodged from the surgical needle 39 as a result of the non-destructive test, the control system computer 46 is flagged so that the disarmed needle 39 will be ejected at the pull-test station. The dislodged suture strand will be drawn into a vacuum assembly (not shown) and the needle 39 will be ejected by a needle stripper assembly 190 shown generally in FIG. 10(a) and in detail in FIG. 16. As shown in FIG. 10(a), needle stripper solenoid 190(a) will be actuated by a control signal output from the control system computer 46 to extend needle stripper pin 192(a) to a space 188 (illustrated in FIG. 14(b)) between the needle 39 and the face of the universal gripper 155. Thus, when the needle is in its relaxed state on the universal gripper 155 and the minimum pull-test fails, the needle stripper pin 192(a) is extended to remove the needle from the universal gripper 155. The needle will fall and be collected by appropriate collection means (not shown) located at the pull-test station.

After the pull test, whether successful or unsuccessful, the apparatus prepares for the next armed needle to be pull-tested. Slide block assembly 472 and retracted gripper jaws 325a,b are pushed back up with respect to the fixed slide mount frame 426 to the home position by an appropriate upward force supplied by the air cylinder 479 as controlled by the control system computer 46. At this time, another data signal may be sent for storage in a database maintained by the control system computer that indicates that the pull-test performed on the particular needle 39 was either successful or unsuccessful, together with a data signal which represents the loading on load cell 435. A signal flag may also be sent which indicates that a needle suture assembly is being conveyed downstream for bundling thereof.

In the preferred embodiment of the invention, the load cell 435, illustrated in FIGS. 20 and 22(*a*) 22(*b*) is a piezoelectric transducer that measures the force applied by the slide block assembly to the needle-suture assembly 39. The force is received by the needle v-plate arm at 436(*a*), and transmitted to load cell 435 mounted underneath the v-plate arm 436 by virtue of the pivotal mounting of the v-plate needle arm on bolt 438. This single point mount enables an easy parts change for needle v-plate arm when different needle or suture sizes call for a different opening at 436(*a*). The transducer load cell 435 may be interfaced with the control system computer 46 by conventional means, and, in the preferred embodiment, is a 25 lb. transducer manufactured by Techniques Co. (Model No. MDB-25PH). The forces applied to the suture 39 and measured by the load cell transducer 435 during the destructive pull-testing may be stored for statistical purposes or for real-time monitoring during a swage die setup routine that may take place when a new batch of surgical needles are to be swaged. For instance, if the non-destructive pull-tests fail and the force measured by the transducer 435 is determined to be at the low end of a predetermined range, then the control system computer 46 will acknowledge this and send appropriate signals to the upstream swaging assembly described previously causing the fixed swaging die 374 to be advanced an incremental amount toward the moveable swage die 373, resulting in subsequent swages being stronger. Likewise, if the non-destructive pull-test passes, i.e., the forces measured by the transducer are determined to be between a minimum and maximum load, then no die adjustment need be made.

As previously mentioned, the automatic pull-test assembly 400 is used to perform a minimum pull-test upon every armed surgical needle indexed thereto prior to automatic packaging thereof. A destructive pull-testing of the armed surgical needle is performed at a parts change set up and at every nth needle indexed thereafter. The purpose of performing a destructive pull-test is to set the swage dies located at the upstream swaging station for correct maximum swage pull-out value. This is by necessity a destructive test, and the test frequency, which is programmable, is set high enough to maintain control of the operation, but low enough to avoid excessive product waste. In the preferred embodiment, this frequency may be set at every 50th needle, but could be every 75th or 100th needle.

Another purpose of the destructive pull test is to aid in installing a new swage die set during a changeover procedure, which is a procedure that is used to prepare the needle swaging apparatus (swage dies) for processing a new batch of needles when they are of a different size from a previously processed batch. Contrary to the non-destructive pull-test described above, the pull-test apparatus is programmed for 100% destructive test of a swaged needle, while the swaging assembly is operating and feeding the armed needles to the pull-test station. The die adjustment system at the upstream swaging assembly will receive a signal from the computer 46 transducer load cell 335, at each machine cycle, and quickly perform a correct adjustment of the swage dies.

Destructive test pull-out values are recorded in the system computer 46 and are used to compute statistical process control information which is fed back to the machine operator through display screens.

Destructive pull testing of the armed surgical needle 39 is accomplished similarly as described herein above with respect to the minimum pull test, but with a second pair of gripper jaws 426*a,b* and destructive test air cylinder 474. However, the fundamental difference between the tests is a Nixed mechanical stroke that is always strong enough to pull the suture out of the needle. This destructive stroke replaces the variable 2 to 30 ounce force of the minimum pull test routine.

As shown in FIG. 21(*a*), a second air cylinder 474 located opposite air cylinder 479 is programmed to provide a fixed stroke against load balancing plate 424 from the home position shown in FIG. 21(*a*). This results in a downward vertical displacement of lower slide block assembly 472 from the position shown in FIG. 21(*a*). This also results in a downward force upon slide rods 472(*a*) and(*b*), which moves the gripper assembly 470 downwardly, including gripper jaws 426*a,b* and the suture gripped therein, in the direction of the arrow "A" as shown in FIG. 21(*a*). The air pressure supplied to cylinder 474 is set high enough to always pull the suture out of needle 39. This stroke is limited by the bottom portion of slide assembly 472 striking the top of stationary frame 426. The destructive pull test jaws 426*a,b* are serrated on their gripping surface, as shown in FIG. 21(*a*) to ensure a positive non-slip grip on the suture during the destruct cycle. Further, the destruct gripper jaws 426*a,b* are driven by a pair of air cylinders 441,442 through angled offset arms 443,444.

The axis of reciprocation for each of the sets of jaws is illustrated in FIG. 21(*a*), with the axis for the non-destruct gripper at 445, and the axis of reciprocation for the destructive gripper jaws illustrated in FIG. 21(*a*) at 446.

The force necessary to accomplish the destructive pull-test is measured by the piezoelectric load cell transducer 435 as discussed above, and data representing this force is sent to the control computer 46. If it is determined by the process control algorithm (described below) that the destructive pull-test forces as measured by the transducer load cell are lower than a predetermined range of pull-test values, the control system computer 46 will send out appropriate control signals to increase the swaging die stroke applied when swaging the suture to the needle at the upstream swaging station. If it is determined that the destructive pull-Lest forces as measured by the transducer load cell are higher than the predetermined range, the control system computer 46 will send out appropriate control signals to the upstream swaging assembly to move a fixed swage die a small incremental distance away from the moveable swage jaw, thereby decreasing the swaging pressure applied when swaging the suture to the needle.

Since the destructive pull-test necessarily results in the suture becoming dislodged from the needle 39, the needle 39 is again removed from the grip of the universal gripper 155 by the needle stripper pin 192(*a*) as described above. Subsequently, the gripper jaws 426*a,b* are retracted to their open positions and air cylinder 479 provides the upward force to restore the gripping assembly 470 and slide block assembly 472 back to their normal position in preparation for the next pull-test.

The control system for the pull test procedure may be the procedure particularly described in U.S. Ser. No. 08/804,476 entitled "Method and System for Establishing and Monitoring a Needle Swaging Procedure," filed Feb. 21, 1997, the disclosure of which is incorporated herein by reference thereto.

Off Load Dial Assembly For Needles and Sutures

Figure 17:
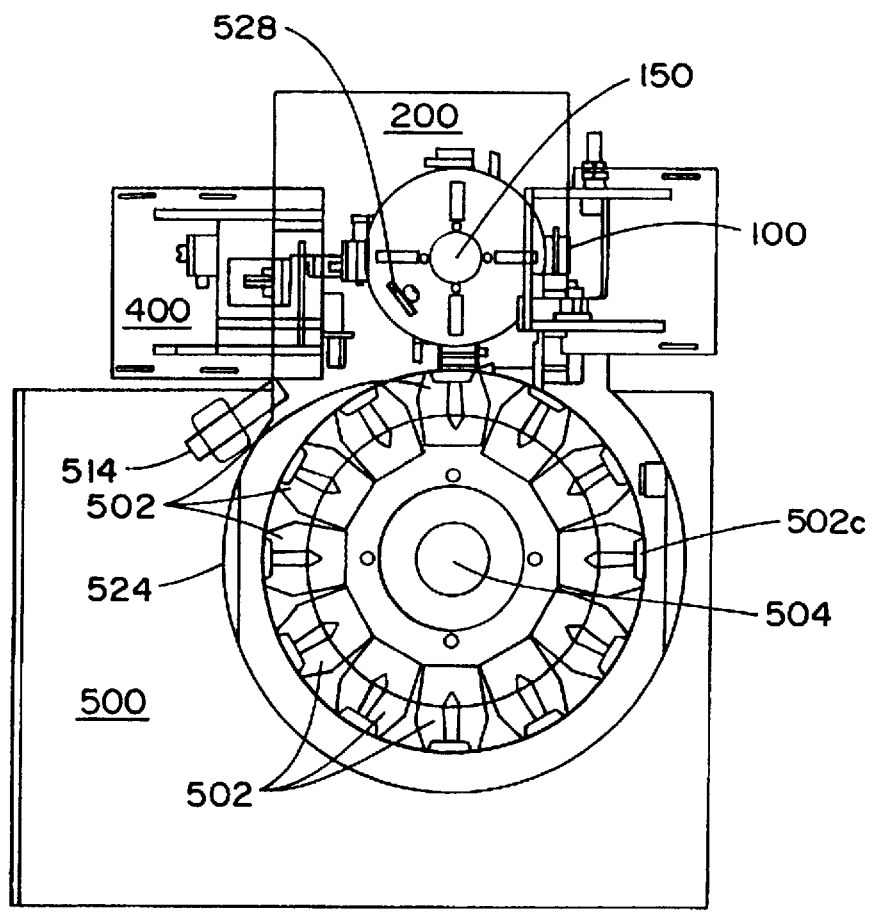
FIG. 17 is a top plan view of the needle bundling station of the present invention illustrating a plurality of compartments, each of which receives a predetermined number of needle and suture assemblies.

The offload station 500 is more particularly illustrated and described with respect to FIGS. 17 and 18–18(b) in which a plurality of needle buckets 502 are circumferentially arranged on a rotatable turntable 504 to be indexed under the collection point 506 defined by an intercept axis of a needle stripper 190 and the face of the universal gripper 155. As the needles are stripped from the universal gripper, they fall into a needle collection bucket which collects the needle inside the bucket, and most of the suture outside the bucket.

One needle stripper assembly 190 is illustrated in FIG. 16, which stripper includes a reciprocating stripping pin 192, which is spring biased inwardly by spring 193, and reciprocated outwardly by pneumatic motor 194 to engage the needle to be stripped. The stripping assemblies are secured in position by means of a bracket 191 which is bolted to the frame of the apparatus.

The present invention includes a pair of needle strippers 190a,190b, the locations of which are illustrated in FIG. 10(a) adjacent the circumference of the swage dial plate 110. Needle stripper assemblies 190(a),(b) are mounted to the frame of the stand alone swage machine by means of brackets 191a,191b to provide a longitudinal axis of reciprocation for the needle stripping pins 192a,b that is tangential to the circumference described by the face of the universal grippers 155. When the needle stripper pins 192 are retracted, as illustrated in FIG. 16, the universal gripper passes the needle stripping station without engagement. However, when the needle stripping pins are reciprocated outwardly, they intercept the path of needle 39 and are positioned to reciprocate into a space 188 (illustrated in FIGS. 14(b) and 15) defined between the face of the universal gripper 155 and the needle 39. Simultaneously therewith, the plunger 170 on the universal gripper is depressed by one of the offload cams 172 to open the jaws 146,148 of the universal gripper and enable the needle to be stripped from the universal gripper.

One needle stripper is used at the pull test station to remove needles that have failed the suture pull test, and a second is used at the off load station to insure a positive removal of the needle and suture assembly from the universal gripper at the off load station.

The needle stripper assembly 190(a) illustrated in FIG. 10(a) is used to remove needles that have failed the pull test at the pull test station 400. The needle stripper assembly 190(b) is used to remove the needle and suture assembly from the universal gripper for bundling in the offload station 500.

The needle bucket of the present invention is illustrated in FIGS. 18–18(b), wherein FIG. 18 is a side view illustrating the a side view of the bucket and the radial reciprocation of the needle bucket, with FIG. 18(a) illustrating a front view of the bucket and FIG. 18(b) illustrating a top view of the bucket.

As illustrated in FIG. 18, dotted line axis A illustrates the circumferential path of the needle in a horizontal plane, while carried by the universal gripper, while axis B and C illustrate the the radial reciprocation of the universal gripper 155 mounted on the swage dial. The needle stripping pin 192b engages the needle at the intersection of axis A and C at intersect 506 causing the needle to drop into the needle bucket 502. The needle falls into the bucket with the suture draped over a comb-like face 520 which holds the suture and assists in preventing entanglement of the sutures when they are removed from the needle bucket. Most of the suture remains outside the bucket, and is captured within a suture shroud 524, illustrated in FIG. 17. The suture shroud 524 guides the unsupported end of the suture and prevents entanglement with the moving parts of the apparatus below the circumferential path described by the universal gripper. In addition, a stream of deionized air may be provided at this station to assist in the orderly collection of the sutures following the swage assembly.

Each of the needle buckets includes a second comb-like surface 522 on one side of the bucket, and an upstanding extended wall portion 526 on the far side of the collection bucket to assist in capturing any late dropping needles.

Each of the needle buckets 502 is spring mounted for radial reciprocation on turntable 504 by means of a spring loaded reciprocating mount 508 which nominally biases the needle bucket 502 inwardly. When the needle bucket has arrived at the offload position, the bucket 502 is reciprocated outwardly as illustrated in FIG. 18b by a pneumatic motor 510 to the position 502b illustrated in FIG. 18.

FIG. 17 also illustrates a detector 514 which is focused on a reflector plate 528 under the swage dial assembly 150 that is triggered by a passing suture to actuate the needle stripping assembly 190(b).

After a predetermined number of needle and suture assemblies have been collected in the needle bucket 502, the needle bucket 502 is reciprocated inwardly by relaxing air motor 510 and the turntable 504 is indexed to position the next available needle bucket 502 under the off load station. While 12 offload buckets 502 have been illustrated in FIG. 17(a), it is understood that a smaller number of buckets could be used if desired.

After a needle bucket 502 has been filled with a predetermined number of needle and suture assemblies, and rotated to the position illustrated at 502(c) in FIG. 17, the bundle of needle and suture assemblies may be removed for subsequent handling and packaging.

As is readily apparent to one skilled in the art, many variations on the above described embodiment are possible. The foregoing description is exemplary only and not to be construed as limiting the scope of the invention, which is defined in the claims, as follows.

What is claimed:

1. An apparatus for automatically testing the swage bond strength of a surgical needle-suture assembly, wherein the assembly has a suture depending from a suture receiving end of a surgical needle, said apparatus comprising:

(a) a needle v-blade arm for supporting said suture receiving end of said surgical needle-suture assembly when a positive downward force of predetermined value is applied to said suture:

(b) a universal gripper for releasably engaging said surgical needle-suture assembly for transport to and from said apparatus and for positioning said needle-suture assembly on said needle v-blade arm with said suture strand depending from said needle v-blade arm;

(c) a non-destructive test assembly having a pair of non-destructive gripping jaws for positively gripping said suture strand at a first position below said v-blade arm, said non-destructive gripping assembly including a slide block means for applying said positive downward force of predetermined value to said gripped suture to thereby test the strength of said swage bond; and (d) a destructive test assembly having a pair of destructive gripping jaws for positively gripping said suture to pull said suture from said surgical needle.

2. The apparatus for automatically testing the swage bond strength of a needle-suture assembly according to claim 1 wherein said slide block means for applying said positive downward force includes a mass of predetermined weight and an adjustable tension device.

3. The apparatus for automatically testing the swage bond strength of a needle-suture assembly according to claim 2 wherein said non-destructive gripping jaws and said slide block means are slidably mounted along a fixed mounting frame, said fixed mounting means positioned substantially parallel with a vertical axis defined by said suture.

4. The apparatus for automatically testing the swage bond strength of a needle-suture assembly according to claim 3 which further includes a relaxable drive for maintaining said gripping means and said slide block means at a first home position along said mounting frame prior to applying said positive downward force to said gripped suture.

5. The apparatus for automatically testing the swage bond strength of a needle-suture assembly according to claim 4 wherein said relaxable drive includes a first air cylinder for applying pressure against said slide block means to maintain said non-destructive gripping means and said slide block means thereof at said first home position.

6. The apparatus for automatically testing the swage bond strength of a needle according to claim 5 wherein said pressure applied to said first side of said slide block means is relaxed to enable said slide block means to slide along said mounting means to a second position that is lower than said first position to apply a positive pre-determined downward force to said gripped suture.

7. The apparatus for automatically testing the swage bond strength of an needle-suture assembly according to claim 2, wherein said slide block means further includes a first means for controlling the application of said downward force applied to said suture strand.

8. The apparatus for automatically testing the swage bond strength of a needle-suture assembly according to claim 7, wherein said first means for controlling the application of said downward force is a spring tension device.

9. The apparatus for automatically testing the swage bond strength of a needle-suture assembly according to claim 1 wherein said destructive test assembly further includes a destructive test air cylinder which applies a fixed downward stroke to said slide block means for destructive tests.

10. The apparatus for automatically testing the swage bond strength of an needle-suture assembly according to claim 1, wherein said non-destructive gripping means includes a pair of retractable gripping jaws.

11. The apparatus for automatically testing the swage bond strength of an needle-suture assembly according to claim 1, which further includes a transducer for measuring the value of said positive downward force applied by said slide block means to said gripped suture.

12. The apparatus for automatically testing the swage bond strength of an needle-suture assembly according to claim 11, wherein said transducer is a load cell which measures a force generated by said needle v-blade arm when said positive downward force is applied to said gripped suture.

13. The apparatus for automatically testing the swage bond strength of a needle-suture assembly according to claim 11 further including a computer control means connected to a detector which outputs a test fail signal if said suture is pulled from said needle after application of said positive downward force.

14. The apparatus for automatically testing the swage bond of said needle-suture assembly according to claim 13, said apparatus further including a needle stripper for removing said needle from said gripping means upon receipt of said test fail signal from said computer control means.

15. The apparatus for automatically testing the swage bond of said a needle-suture assembly according to claim 1, wherein said universal gripper is opened to release its engagement of said needle as said non-destructive gripping means applies said positive downward force of predetermined value to said suture to thereby test the strength of said swage bond.

16. The apparatus for automatically testing the swage bond of said needle-suture assembly according to claim 1 in which said destructive test assembly further includes an air cylinder for applying a second positive downward force against a second side of said slide block means that is sufficient to dislodge said suture from said needle.

17. The apparatus for automatically testing the swage bond strength of an needle-suture assembly according to claim 16, which further includes a transducer for measuring the value of said second positive downward force applied by said destructive test assembly to said suture.

18. The apparatus for automatically testing the swage bond strength of an needle-suture assembly according to claim 17, wherein said transducer includes a load cell for measuring the force applied by said needle v-blade needle support arm when said positive downward force is applied to said suture.

19. The apparatus for automatically testing the swage bond strength of a needle-suture assembly according to claim 18 which further includes a computer control means connected to said transducer means, said transducer means outputting a data value of said destructive test to said computer means as said suture becomes dislodged from said needle after application of said second positive downward force.

20. The apparatus for automatically testing the swage bond strength of a needle-suture assembly according to claim 19 wherein said computer control means utilizes said measured value of said second positive downward force for process control in a swage apparatus.

21. A method for automatically testing the swage bond of a surgical needle-suture assembly wherein the assembly has a suture swaged to a suture receiving end of a surgical needle and depending therefrom, said method comprising the steps of:

(a) positioning the suture receiving end of said needle-suture assembly on a v-blade arm for supporting said needle with a universal gripper means in an oriented position above said v-blade arm;

(b) positively gripping said depending suture strand at a first position below said v-blade arm with a non-destructive gripper means, said non-destructive gripper means having an off-set weight attached thereto;

(c) setting a first positive downward force by means of an adjustable tension device; and (d) applying the first positive downward force upon said suture strand gripped by said non-destructive gripper means.

22. The method for automatically testing the swage bond strength of a surgical needle-suture assembly according to claim 21 wherein step (d) further comprises the step of releasing said needle from the grip of said universal gripper means prior to applying said first positive downward force.

23. The method for automatically testing the swage bond strength of a surgical needle-suture assembly according to claim 22 further including the step of measuring the value of said first positive downward force applied to said suture strand.

24. The method for automatically testing the swage bond strength of a surgical needle-suture assembly according to claim 23 further including the step of comparing said measured force value with a predetermined value and generating a test fail signal if the measured value is not within a predetermined range.

25. The method for automatically testing the swage bond strength of a surgical needle-suture assembly according to claim 21 further including the step of destructively testing the swage bond by destructively pulling said suture from said surgical needle and measuring the force applied at the moment of failure.

26. The method for automatically testing the swage bond strength of a surgical needle-suture assembly according to claim 25 further including the step of comparing said destructive test measured force value with a predetermined value and generating a repeat test signal if the measured value is not within a predetermined range.

* * * * *